United States Patent [19]

Magerlein

[11] 3,984,393

[45] Oct. 5, 1976

[54] AMINOGLYCOSIDE ANTIBIOTICS

[75] Inventor: Barney J. Magerlein, Portage, Mich.

[73] Assignee: The Upjohn Company, Kalamazoo, Mich.

[22] Filed: Sept. 8, 1975

[21] Appl. No.: 611,350

[52] U.S. Cl.............................. 536/17; 424/180; 536/4; 536/10; 536/12
[51] Int. Cl.².................................. C07H 15/22
[58] Field of Search.................. 260/210 AB, 210 K

[56] References Cited
UNITED STATES PATENTS

| | | | |
|---|---|---|---|
| 3,753,973 | 8/1973 | Umezawa et al. | 260/210 AB |
| 3,792,037 | 2/1974 | Kawaguchi et al. | 260/210 AB |
| 3,872,079 | 3/1975 | Naito et al. | 260/210 AB |
| 3,886,139 | 5/1975 | Naito et al. | 260/210 AB |
| 3,893,997 | 7/1975 | Cooper et al. | 260/210 AB |

OTHER PUBLICATIONS

Umezawa et al., "Bull. Chem. Soc. Japan," vol. 42, pp. 537–541, 1969.
Ogawa et al., "Tetrahedron Letters," vol. 46, pp. 4013–4016, 1974.

Primary Examiner—Johnnie R. Brown
Attorney, Agent, or Firm—Roman Saliwanchik

[57] ABSTRACT 6-0- and 3'-0-D-glycosyl analogs of 4-0-(α-D-glycosyl)-2-deoxystreptamine, 6-0- and 3'-0-D-glycosyl ortho esters of 4-0-(α-D-glycosyl)-2-deoxystreptamine, novel aminoglycoside antibiotics, and novel intermediates are prepared by a new chemical process. The compounds have utility as antibacterial agents or as intermediates to make antibacterially-active compounds.

32 Claims, No Drawings

AMINOGLYCOSIDE ANTIBIOTICS

BACKGROUND OF THE INVENTION

Microbially produced aminoglycosides, possessing the 2-deoxystreptamine moiety, have either a pentofuranosyl substituent at the 5–O position or a hexopyranosyl substituent at the 6–O position. Examples of antibiotics with a pentofuranosyl substituent at the 5–O position are paromomycin, neomycin, lividomycin and ribostamycin. Examples of antibiotics having a hexopyranosyl substituent at the 6–O position are kanamycin B and gentamicin $C_{1a}$. Subsequent to the subject invention, a publication by T. Ogawa, T. Takamoto and S. Hanessian, Tetrahedron Letters, 46, 4013 (1974), discloses the preparation of a 6–O-pentofuranosylparomamine analog. Paromamine differs from neamine by having a hydroxyl at the 6' position instead of an amino moiety.

BRIEF SUMMARY OF THE INVENTION

The subject invention concerns novel aminoglycosides, nontoxic pharmaceutically acceptable acid addition salts thereof, intermediates, and a novel process for their preparation. More particularly, the subject invention concerns 6-O- and 3'-O-D-glycosyl analogs of 4-O-(α-D-glycosyl)-2-deoxystreptamine, novel aminoglycoside antibiotics, novel intermediates, and a chemical process for the preparation thereof. The process comprises essentially six steps: (1) the aminogroups of the starting aglycone, are blocked; (2) the 5,6-hydroxyls are blocked as the ketal; (3) the 3',4'-hydroxyls are acylated; (4) the ketal group is removed; (5) the desired sugar moiety is added using a variation of the well-known Koenigs-Knorr glycosylation reaction; and, (6) the blocking groups are removed to afford the new aminoglycoside antibiotic. When the 3'-O-D-glycosyl analog is made, Step 3 and Step 4 are omitted.

The subject invention process is novel and advantageous for the preparation of the new aminoglycosides for several reasons. The blocking of the amino groups as the trifluoroacetates departs from the usual chemical approach using the carbobenzyloxy group as a blocking agent. The trifluoroacetyl group has advantages over the carbobenzyloxy group in its preparation; it is easier to remove (mild alkali vs. hydrogenolysis); it imparts much greater solubility in organic solvents thus permitting easier manipulation and purification (for example, with chromatography); and, since it is more volatile, intermediates can be examined by vapor phase chromatography, thus facilitating the synthesis. Further, the very selective formation of a ketal is surprising and unexpected in view of prior work in the art. For example, Umezawa, et al., Bull Chem. Soc. Japan, 42, 537 (1969), when working with carbobenzyloxy-blocked neamine, formed a difficultly separable mixture of monoketals.

The novel six step process, briefly described above, can be schematically depicted as follows showing, for convenience, a specific sugar. However, it is to be understood that other sugars, as disclosed herein, can be used to make novel aminoglycoside antibiotics. Also, for convenience, neamine is the depicted aglycone. The scope of 4-O-(α-D-glycosyl)-2-deoxystreptamine is given infra.

Step 1.

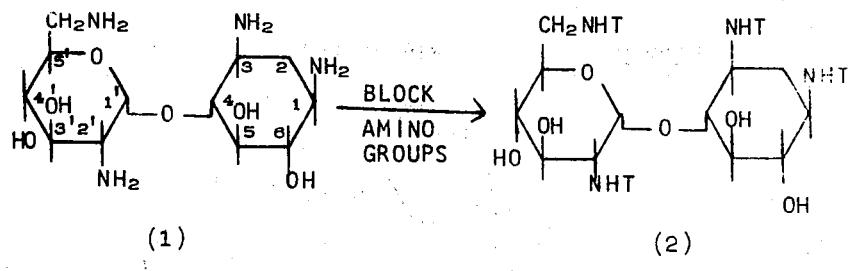

T = amino blocking group

Step 2.

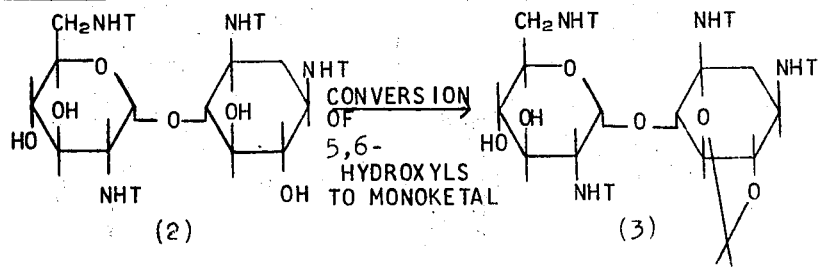

Step 3.
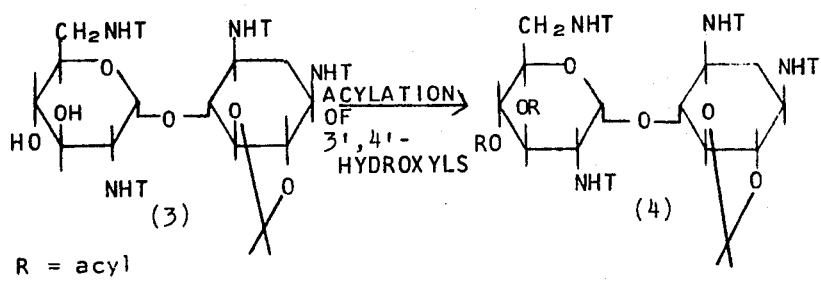
R = acyl
Step 4.
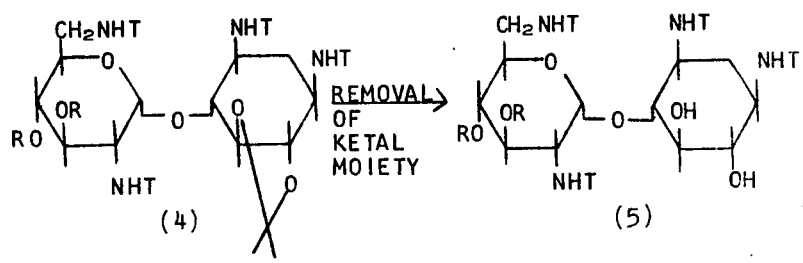
Step 5. KOENIGS-KNORR GLYCOSYLATION
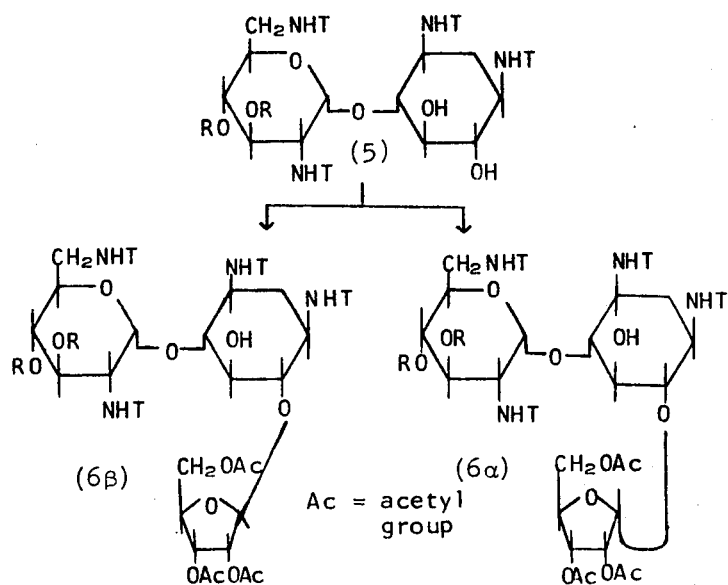
Ac = acetyl group Step 6.    REMOVAL OF PROTECTING GROUPS

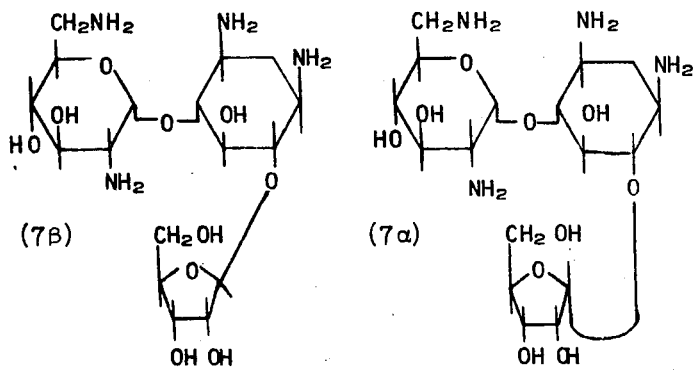

Novel ortho esters are prepared by reacting compound 5 with the desired sugar moiety in the presence of a strong base. This reaction can be schematically depicted as follows:

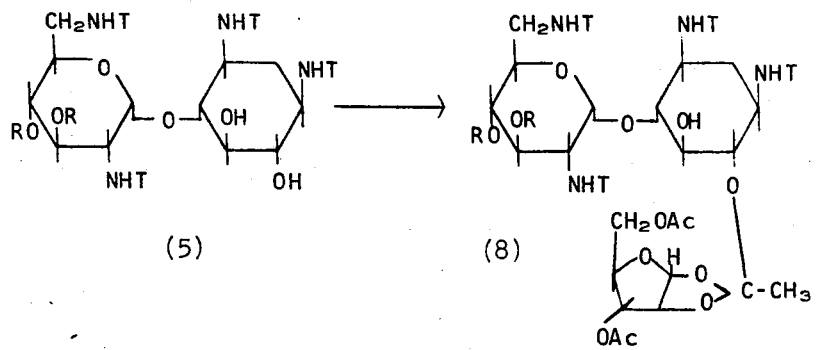

The protecting groups on compound 8 are then removed following the procedures of Step 6, above, to afford the ortho ester. Substitution of the sugar at the 3-O- position ortho esters is accomplished by omitting the acylation step (Step 3) and reacting compound 3 with the desired sugar moiety in the presence of a strong base. The resulting compound is then subjected to mild acid hydrolysis to remove the ketal group at the 5,6 position. The remaining acyl groups on the sugar moiety are removed by alkaline hydrolysis.

DETAILED DESCRIPTION OF THE INVENTION

Novel aminoglycoside antibiotics, which are 6-O- and 3'-O-glycosyl analogs of 4-O-(α-D-glycosyl)-2-deoxystreptamine and 6-O- and 3'-O-glycosyl ortho esters of 4-O-(α-D-glycosyl)-2-deoxystreptamine can be prepared by the novel process described herein.

The following 4-O-(α-D-glycosyl)-2-deoxystreptamines can be used as the starting material aglycone in addition to neamine, disclosed above:

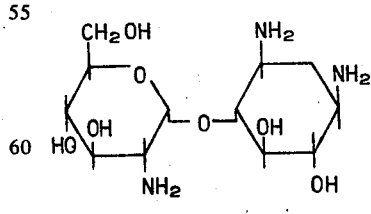

PAROMAMINE

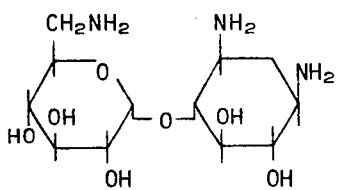 KANAMINE
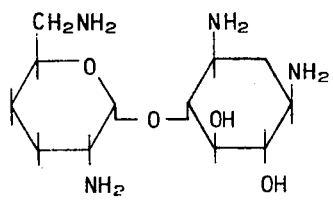 GENTAMINE $C_{1a}$
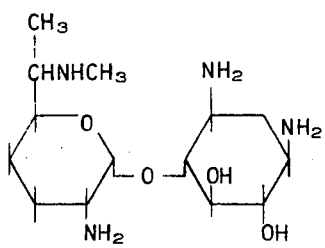 GENTAMINE $C_1$
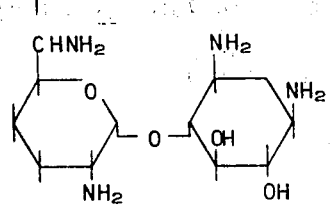 GENTAMINE $C_2$
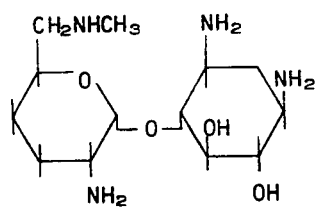 GENTAMINE $C_{2b}$
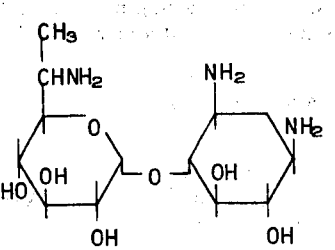 GENTAMINE $B_1$
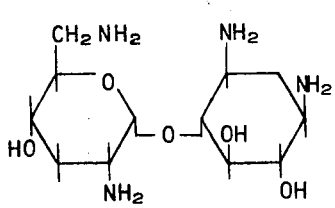 NEBRAMINE (Tobramine)

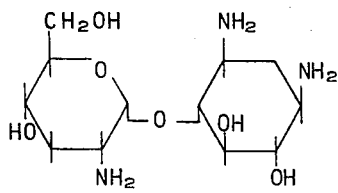

LIVIDAMINE

The subject invention process yields novel 6-O- and 3'-O-D-glycosyl analogs of neamine and paromamine. Since the remaining 4-O-(α-D-glycosyl)-2-deoxystreptamines, as disclosed above, either contain 3 hydroxyls in the B ring (left-hand ring) or lack a C-3 hydroxyl, only novel 6-O-D-glycosyl analogs of these aglycones are made.

The starting material aglycones are well known in the art and can be prepared by the procedures given in the following publications:

Neamine (Neomycin A): Prep. from neomycin B, U.S. 2,691,675. Synthesis from paromine, S. Umezawa and K. Tatsuta, Bull. Chem. Soc. Japan, 40, 2371–75 (1967).

Paromamine: S. Umezawa and S. Koto, Bull. Chem. Soc. Japan, 39, 2014 (1966).

Kanamine: S. Umezawa, T. Tsuchiya, J. Antib., 15, 51–52 (1962).

Nebramine (Tobramine): K. F. Koch, J. A. Rhoades, E. W. Hagaman and E. Wenkert, J. Amer. Chem. Soc., 96, 3300–05 (1974). [however have typographical error between neamine and nebramine]

Lividamine: T. Oda, T. Mori and Y. Kyotani, J. Antib., 24, 503–10 (1971).

Gentamine $C_{1a}$, $C_1$ and $C_2$: D. J. Cooper, P. J. L. Daniels, M. D. Yudis, H. M. Marigliano and (in part) R. D. Gulkrie and S. T. K. Bukari, J. Chem. Soc. (C), 3126–29 (1971). More data J. B. Morton, R. C. Long, P. J. L. Daniels, R. W. Tkach and J. H. Goldstein, J. Amer. Chem. Soc., 95, 7464–69 (1973).

Gentamine $C_{2b}$: P. J. L. Daniels, C. Luce, T. L. Nagathusushan, R. S. Faut, D. Schumacher, H. Kermann and J. Ilavasky, J. Antib., 28, 35 (1975).

R. S. Egan, R. L. DeVault, S. L. Mueller, M. I. Levenberg, A. C. Sinclair and R. S. Stanasyck, J. Antib., 28, 29–34 (1975).

Gentamine $B_1$: Belg. Pat. No. 768,796, June 21, 1971.

In the novel process, the amino groups in the aglycone starting material are first blocked by a suitable blocking group. The preferred blocking group is trifluoroacetyl. Thus, neamine (1), in the preferred embodiment of this process step, hereinafter referred to as Step 1 for convenience, is reacted, as a suspension in acetonitrile, with trifluoroacetic anhydride in the presence of an organic base, for example, triethylamine. The trifluoroacetic anhydride is added to the neamine suspension at 15°± 5° over a period of 30 minutes. The reaction mixture is stirred at ambient temperature for about one hour and the solvent is then evaporated in vacuo. The desired product (2) is then recovered by solvent extraction with ethyl acetate and crystallization from ethanol.

Suitable substitutions for trifluoroacetic anhydride in Step 1 are pentafluoropropionic anhydride and the ethylthio ester of trifluoroacetic acid, S-ethyl trifluorothioacetate. A suitable replacement for acetonitrile in Step 1 is ethyl acetate or other solvents in which the reaction products are soluble. The reaction can be carried on over a temperature range of 0° to the boiling point of the reactants. Those skilled in the art recognize that the lower the reaction temperature, the longer the reaction time. The recovery of the product from Step 1 is accomplished by well-known art procedures. In place of ethyl acetate, which is preferred as the extraction solvent, other water-insoluble solvents, for example butyl acetate, and the like, can be used.

Step 2 of the invention process is concerned with forming the 5,6-ketal of the compound obtained in Step 1. In a preferred Step 2 process, product (2) in acetonitrile and 2,2-dimethoxypropane containing trifluoroacetic acid is heated at reflux for about ¾ of an hour. Thereafter, the basic resin IRA-45 (OH⁻) is added to the reaction solution to remove the acid catalyst. Monoketal compound (3) is recovered from the reaction by well-known chromatographic techniques.

The 2,2-dimethoxypropane of Step 2 can be replaced by other dialkoxy lower alkanes where in the alkoxy and lower alkane can be from 1 to 8 carbon atoms, inclusive. Preferably, the lower alkane radicals are the same, but they can be different. Examples of suitable dialkoxy lower alkanes are 2,2-diethoxypropane, 2,2-dipropoxypropane, 2,2-dibutoxypropane, 2,2-dipentoxypropane, 2,2-dihexoxypropane, 2,2-diheptoxypropane, 2,2-dioctoxypropane, dimethoxymethane, 3,3-dimethoxypentane, 4,4-dimethoxyheptane, and the like, and 2-ethoxy-2-methoxypropane, and the like.

The acid catalyst trifluoroacetic acid in Step 2 can be replaced by p-toluenesulfonic acid or strong inorganic acids, for example, HCl, $H_2SO_4$, and the like. It is desirable to control the amount of acid catalyst used since an excess amount will result in the formation of the diketal compound instead of the desired monoketal. If the diketal is formed, it can be converted to the monoketal by selective methanolysis procedures known in the art employing methanol and an acid catalyst, for example, trifluoroacetic acid.

In the preferred process, the removal of the acid catalyst in Step 2 upon completion of the reaction is accomplished by mixing the reaction solution with Amberlite IRA-45 (OH⁻), a basic resin. Other resins which can be used are obtained by chloromethylating by the procedure given on pages 88 and 97 of Kunin, Ion Exchange Resins, 2nd ed. (1958), John Wiley and Sons, Inc., polystyrene crosslinked, if desired, with divinylbenzene, prepared by the procedure given on page 84 of Kunin, supra, and quaternizing with trimethylamine or dimethylethanolamine by the procedure given on page 97 of Kunin, supra. Anion exchange resins of this type are marketed under the tradenames Dowex 2, Dowex 20, Amberlite IRA-400 (OH⁻), Amberlite IRA-410 (OH⁻), Amberlite IRA-401 (OH⁻), Duolite A-102 and Permutit S.1.

The acid catalyst of Step 2 also can be removed by the use of insoluble basic salts, for example, barium carbonate, lead carbonate, and the like.

The acylation of the 3' and 4'-hydroxyls of Step 3 can be carried out by acylating procedures well-known in the art. The preferred process uses p-nitrobenzoyl chloride as the acylating agent because it gives the acylated product (4) which produces ultraviolet light visibility on thin layer chromatography during the Koenigs-Knorr glycosylation of Step 5. However, other acylating agents can be used to give the acylated product. The acylation is carried out in the presence of an acid-binding agent. Suitable acid-binding agents include amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, hydroxy-, amino-, cyano-, thiocyano-, and lower alkoxyhydrocarbon carboxylic acids include hydrocarboncarboxylic acids as given above which are substituted by one or more of halogen, nitro, hydroxy, amino, cyano, or thiocyano, or loweralkoxy, advantageously loweralkoxy of not more than six carbon atoms, for example, methoxy, ethoxy, propoxy, butoxy, amyloxy, hexyloxy groups, and isomeric forms thereof. Examples of such substituted hydrocarbon carboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicyclic acid;
p-hydroxybenzoic acid;
β-resorcylic acid;
gallic acid;
veratric acid;
trimethoxybenzoic acid;
trimethoxycinnamic acid;
4,4′-dichlorobenzilic acid;
o-, m-, p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate); and the like.

Product (4), obtained in Step 3, is subjected to mild acid hydrolysis to remove the ketal group. In the preferred process of Step 4, a solution of (4) in about a 66% acetic acid solution is warmed at 65° for about 4 hours. Recovery of the desired product (5) is accomplished by removal of the solvent and use of standard chromatographic procedures.

The acetic acid of Step 4 can be replaced by other mild acids, for example, propionic and oxalic, which will not cause ester hydrolysis. If a stronger acid is used, for example, trifluoroacetic acid, hydrochloric sulfuric or trichloroacetic acid, then the reaction time will be shorter and the temperature of the reaction lower. The temperature of the reaction can be varied over a range of about 10° to about 100° depending on the acid used.

The glycosylation of product (5) is performed, according to Step 5, by use of the well-known Koenigs-Knorr reaction. It is critical for successful yields in Step 5 that the reaction be conducted under anhydrous conditions. In the preferred process of Step 5, the anhydrous conditions are obtained by distillation of benzene from the reaction mixture and use of an atmosphere of dry $N_2$. In the preferred process of Step 5, a solution of desired sugar moiety in nitromethane-benzene, as the bromide or chloride, and with the hydroxyls blocked by acetyl groups, is reacted with compound (5) in the presence of $Hg(CN)_2$ under reflux to give compound (6).

Alternatively, the hydroxyls of the sugar moiety of Step 5 can be blocked by benzyl groups to give the benzyl ether and these benzyl groups can subsequently be removed by hydrogenolysis:

Nitromethane is the preferred solvent in Step 5 because mercuric cyanide is relatively soluble in this solvent. Other solvents which can be used are ethyl acetate, acetonitrile and dimethylformamide since mercuric cyanide is somewhat soluble in these solvents.

Mercuric cyanide of Step 5 can be replaced by other mercury salts, for example, mercuric bromide, mercuric chloride, mercuric oxide, and the like. Further, silver salts, for example, silver carbonate, silver perchlorate, and the like, can be used in place of mercuric cyanide.

The temperature of the reaction in Step 5 can range from about room temperature to about the boiling point of the solvent used.

An excess of the sugar bromide or chloride is necessary in Step 5 in order to complete the reaction. Thus, the ratio of sugar bromide or chloride to compound (5) should be at least 2:1 and possibly as high as 10:1. A great excess is not desirable since recovery problems will be greater.

Step 6 of the invention process is conducted to simultaneously hydrolyze the esters and amino protecting groups. In a preferred embodiment of Step 6, a solution of compound (6) and 2N NaOH in methanol is heated at reflux for about 15 minutes. The methanol is then removed in vacuo, water is added to the solution, and compound (7) is recovered by subjecting the solution to standard ion exchange procedures. Any strong aqueous alkali, for example, potassium hydroxide, barium hydroxide, ammonium hydroxide, and the like, can be substituted for the sodium hydroxide. The aqueous alkali can be more dilute than 2N but, advantageously, not much stronger so that the protective groups are selectively removed.

The process for preparing ortho esters proceeds from compound (5) to compound (8). In a preferred embodiment of this process, a solution of (5) in triethylamine is reacted with the desired sugar halide at reflux to give compound (8). Any strong organic base, for example, 1,4-bis-(dimethylamino)-naphthalene, can be used instead of triethylamine. The temperature of the reaction can range from 0° - reflux. The protecting groups on compound (8) can be removed following the procedure of Step 6 to afford the desired ortho ester (9). However, care must be taken as the ortho ester is somewhat hydrolyzed by alkali though at a lesser rate than the other groups.

3'O-D-glycosyl ortho esters are prepared in like manner starting with compound (3). The ketal and protective groups are removed as disclosed above.

Novel 1-N-AHBA derivatives of the compounds of the subject invention can be formed by use of processes well known in the art. These derivatives potentiate the antibacterial activity and make the antibiotic more resistant to enzymatic inactivation. Thus, these derivatives can be used for the same antibacterial purposes as the parent compounds.

The novel 1-N-AHBA derivatives of the subject invention can be made of any compound of the invention by reacting such compound with one which contains three to five carbon atoms, has an α-hydroxyl group in the L-configuration, and has an ω-aminogroup. These compounds can be shown as follows wherein neamine, for convenience, is shown as the aglycone:

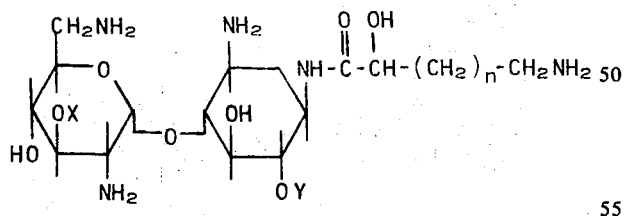

wherein X and Y = H, and substituted glycosyl, except that X and Y are not the same. $n$ is an integer of from 0 to 2, inclusive.

The preparation of the above 1-N-AHBA derivatives can proceed by first blocking the 6'-amino. This can be accomplished by the reaction of the aminoglycoside with N-benzyloxycarbonyloxylsuccinimide in aqueous dimethylformamide. The 6'-N-carbenzoxyamino glycoside thus formed is selectively 1-N-acylated with L(−)γ-benzyloxycarbonylamino-α-hydroxybutyric acid, N-hydroxysuccinimide ester in aqueous ethylene glycol dimethyl ether. The carbobenzoxy groups at 6'-N and at the γ-N can then be removed hydrogenolysis using, for example, palladium on charcoal as catalyst. The above procedure is disclosed in Kawaguchi, Naito, Nakagawa and Fujisawa, *J. Antibiotics*, 25, 695 (1972), and in U.S. Pat. No. 3,781,268.

Other more elegant methods to make 1-N-AHBA derivatives can be used as reviewed by Umezawa in, *Adv. Appl. Microbiol.*, 18, 174 (1973).

Alternatively, the 1-N-AHBA group can be introduced into the starting compound neamine (1). 1-N-AHBA neamine is disclosed in an article by R. Akita et al., *J. Antibiotics*, 26, 365 (1973) and Tsukuira, ibid., p. 351. If this procedure is used, the α-hydroxy would require blocking with p-nitrobenzoyl chloride at the same time as the 3'-O and 4'-O ester is formed. The blocking group can then be removed by the procedures of Step 6, described herein.

Glycosyl halides, as defined by Wolfrom and Szarek, *The Carbohydrates*, Vol. 1A, p. 239, Pigman and Horton editors, Academic Press, New York (1972), are "saccharide derivatives in which the hydroxyl group of the anomeric center of the aldose or ketose is replaced by a halogen atom." This definition is used herein with the following limitations: (a) 5–8 carbon atoms with various configurations of hydroxyl groups; (b) 1-chloro or 1-bromo sugars in either the 1-α or 1-β-halo configuration; (c) hydroxy groups blocked as acylates (acetate or benzoate), or as benzyl ethers; and (d) amino, alkylamino or dialkylamino sugars including, for example, 2-amino-2-deoxy, 3-amino-3-deoxy, 4-amino-4-deoxy, 5-amino-5deoxy, 6-amino-6-deoxy, 2,6-diamino-2,6-dideoxy, and their N-mono and N,N$_1$-dialkyl substitutes. A rather complete disclosure of glycosyl halides can be found in the book *The Amino Sugars*, Vol. 1A, Academic Press, N.Y. (1969) by Jeanloz, and in the publication by L. J. Haynes and F. H. Newth, "Glycosyl Halides And Their Derivatives", *Advances in Carbohydrate Chemistry*, Vol. 10, Academic Press, 1955, pages 247–254.

The generic structure of the glycosyl halides which can be used in the subject invention can be shown as follows:

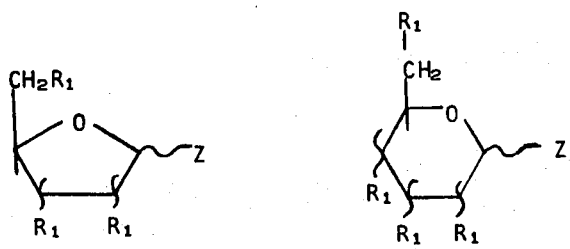

wherein Z is Cl or Br; $R_1$ = OAc,

$OCH_2\phi$, $NHR'$, $NR'$-alkyl; alkyl = 1–5 carbon atoms, inclusive; $R'$ = acyl of from 1 to 8 carbon atoms, inclusive; Ac = acetyl; and

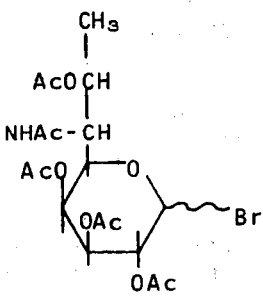

wherein Ac is acetyl.

A sub-generic structure of the glycosyl halides which can be used in the subject invention to make corresponding aminoglycoside antibiotics can be shown as follows:

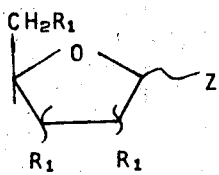 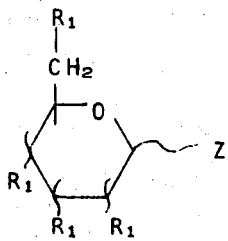

wherein Z is Cl or Br, and $R_1$ is OAc or NHAc wherein Ac is acetyl.

A further sub-generic structure of the glycosyl halides which can be used in the subject invention to make corresponding aminoglycoside antibiotics can be shown as follows:

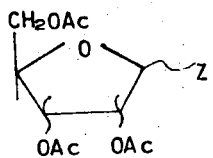 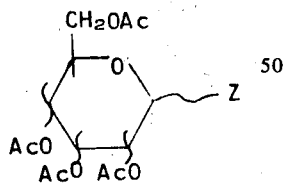

wherein Z is Cl or Br and Ac is acetyl.

Examples of glycosyls (as halides) of sugars which can be used in the subject invention are:

2,3,4,6 Tetra-O-acetyl-α-D-altropyranosyl chloride
2,3,4-Tri-O-acetyl-β-L-arabinopyranosyl chloride -O- and -O-(αO
3,4-Di-O-acetyl-2-deoxy-D-ribopyranosyl chloride
2,3,4,6-Tetra-O-acetyl-α-D-galactopyranosyl chloride
2,3,4,6 Tetra-O-acetyl-β-D-galactopyranosyl chloride
2,3,4,6-Tetra-O-acetyl-α-D-glucopyranosyl chloride
2,3,4,6-Tetra-O-benzoyl-α-D-glucopyranosyl chloride
2,3,4,6-Tetra-O-acetyl-β-D-glucopyranosyl chloride
2,3,4,6-Tetra-O-acetyl-α-D-mannopyranosyl chloride
2,3,4,6-Tetra-O-benzoyl-α-D-mannopyranosyl chloride
2,3,4-Tri-O-acetyl-α-L-rhamnopyranosyl chloride
2,3,4-Tri-O-benzoyl-α-L-rhamnopyranosyl chloride
2,3,5-Tri-O-acetyl-α-D-ribofuranosyl chloride
2,3,4-Tri-O-benzoyl-α-D-ribopyranosyl chloride
2,3,4-Tri-O-acetyl-β-D-ribopyranosyl chloride
2,3,4-Tri-O-benzoyl-β-D-ribopyranosyl chloride
2,3,4-Tri-O-acetyl-α-D-xylopyranosyl chloride
2,3,4-Tri-O-acetyl-β-D-xylopyranosyl chloride
2,3,4-Tri-O-acetyl-6-deoxy-α-D-glucopyranosyl chloride
2,3,4-Tri-O-acetyl-β-D-arabinopyranosyl bromide
2,3,4-Tri-O-benzoyl-β-D-arabinopyranosyl bromide
3,4,6-Tri-O-acetyl-2-deoxy-α-D-glucopyranosyl bromide
3,4,6-Tri-O-benzoyl-2-deoxy-α-D-glucopyranosyl bromide
2,3,4-Tri-O-acetyl-6-deoxy-α-D-glucopyranosyl bromide
1,3,4,5-Tetra-O-acetyl-β-D-fructopyranosyl bromide
1,3,4,5-Tetra-O-benzoyl-β-D-fructopyranosyl bromide
2,3,4,6-Tetra-O-acetyl-α-D-galactopyranosyl bromide
2,3,4,6-Tetra-O-acetyl-α-D-glucopyranosyl bromide
2,3,4-Tri-O-acetyl-6-O-benzoyl-α-D-glucopyranosyl bromide
2,3,4-Tri-O-acetyl-6-O-methyl-α-D-glucopyranosyl bromide
6-O-Acetyl-2,3,4-tri-O-benzyl-α-D-glucopyranosyl bromide
2,3,4,6-Tetra-O-acetyl-α-D-mannopyranosyl bromide
2,3,4,6-Tetra-O-benzoyl-α-D-mannopyranosyl bromide
2,3,4-Tri-O-acetyl-α-L-rhamnopyranosyl bromide
2,3,4-Tri-O-benzoyl-α-L-rhamnopyranosyl bromide
2,3,4-Tri-O-acetyl-β-D-ribopyranosyl bromide
2,3,4-Tri-O-benzoyl-β-D-ribopyranosyl bromide
2,3,4-Tri-O-benzoyl-D-xylopyranosyl bromide
2,3,4-Tri-O-acetyl-L-xylopyranoxyl bromide
2,3,4-Tri-O-benzoyl-L-xylopyranoxyl bromide 2-Acetamido-3,4,6-tri-O-acetyl-2-deoxy-α-D-glucopyranosyl bromide
2-Acetamido-3,4,6-tri-O-acetyl-2-deoxy-α-D-glucopyranosyl chloride
2-Acetamido-3,4,6-tri-O-acetyl-2-deoxy-β-D-glucopyranosyl chloride
2-Benzamido-3,4,6-tri-O-benzoyl-2-deoxy-α-D-glucopyranosyl bromide
3,4,6-Tri-O-acetyl-2-benzamido-2-deoxy-α-D-glucopyranosyl chloride
3,4,6-Tri-O-acetyl-2-[(benzyloxycarbonyl)-amino]-2-deoxy-α-D-glucopyranosyl bromide
3,4,6-Tri-O-acetyl-2-deoxy-2-(2,4-dinitroanilino)-α-D-glucopyranosyl bromide
2-Acetamido-3,4-di-O-acetyl-2-deoxy-D-ribofuranosyl chloride
2-Acetamido-3,4,6-tri-O-acetyl-2-deoxy-D-galactopyranosyl bromide
2-Acetamido-3,4,6-tri-O-acetyl-2-deoxy-α-D-galactopyranosyl chloride
3-Acetamido-2,4,6-tri-O-acetyl-3-deoxy-α-D-mannopyranosyl bromide
3-Acetamido-2,4,6-tri-O-acetyl-3-deoxy-α-D-mannopyranosyl chloride 2,4,6-Tri-O-acetyl-3-[(benzyloxycarbonyl)-amino]-3-deoxy-α-D-glucopyranosyl bromide
2,3,4-Tri-O-acetyl-6-[(benzyloxycarbonyl)-amino]-6-deoxy-α-D-glucopyranosyl bromide
2,4,6-Tri-O-acetyl-3-[(benzyloxycarbonyl)-amino]-3-deoxy-D-glucopyranosyl chloride
2,3,4-Tri-O-acetyl-6-[(benzyloxycarbonyl)-amino]-6-deoxy-D-glucopyranosyl chloride The above are known and available glycosyl halides as disclosed in D. Horton, *Monosaccharide Amino Sugars*, in "The Amino Sugars", Vol. 1A, Editor R. W. Jeanloz, Academic Press, N. Y. (1969), p. 204 and in L. J. Haynes and F. H. Newth, *Advances in Carbohydrate Chemistry*, Vol. 10, Academic Press, 1955, pages 147–154. Other glycosyl halides which can be used in the subject invention are N-acetyl-2,3,4,7-tetra-O-acetyl-α and β-lincosaminyl bromides as disclosed by B. Bannister, *J. Chem. Soc.*, Perkin, 3025 (1972). Still other substituted glycosyl halides which can be used in the subject invention are 3-acetamido-2,4,6-tri-O-benzyl-3-deoxyglucopyranosyl chloride [S. Koto et al., *Bull. Chem. Soc. Japan*, 41, 2765 (1968)]; 2,3,4-tri-O-benzyl-6-(N-benzylacetamido)-6-deoxy-α-D-glucopyranosyl chloride [Koto, ibid.]; 3-acetamido-2,4,6-tri-O-acetyl-3-deoxyglucopyranosyl bromide [Shibahara, et al., *J. Amer. Chem. Soc.*, 94, 4353 (1972)]; and 3,4,6-tri-O-acetyl-2-trifluoroacetamido-2-desoxy-α-D-glucopyranosyl bromide [Meyer zv Reckendorf et al. *Chem Ber.*, 103, 1792 (1970)].

Novel compounds produced by the novel process, hereinafter described in detail, can be shown generically by the formula

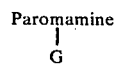

wherein G is a glycosyl attached to the 3' or 6 position of paromamine, said glycosyl of the formulae

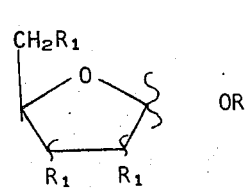 OR 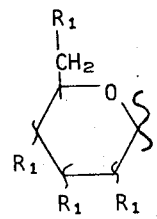

wherein $R_1$ is selected from the group consisting of OH, OAc,

$OCH_2\phi$, $NHR'$, $NR'$ alkyl; wherein alkyl is from 1 to 5 carbon atoms, inclusive; $R'$ is H or acyl of from 1 to 8 carbon atoms, inclusive; Ac is acetyl; and

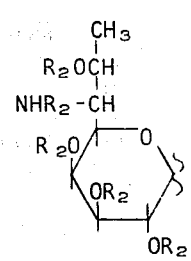

wherein $R_2$ is H or acetyl.

Further novel compounds produced by the novel process, hereinafter described in detail, can be shown generically by the formula

wherein A is a 4-O-(α-D-glycosyl)-2-deoxystreptamine selected from the group consisting of kanamine, gentamine $C_{1a}$, gentamine $C_1$, gentamine $C_2$, gentamine $C_{2b}$, gentamine $B_1$, nebramine, and lividamine, and G is glycosyl attached to the 6 position of said 4-O-(α-D-glycosyl)-2-deoxystreptamine, said glycosyl of the formula

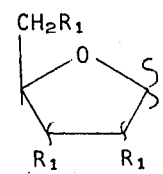

wherein $R_1$ is selected from the group consisting of OH, OAc,

$OCH_2\phi$, $NHR'$, $NR'$ alkyl; wherein alkyl is from 1 to 5 carbon atoms, inclusive; $R'$ is hydrogen or acyl of from 1 to 8 carbon atoms, inclusive; Ac is acetyl,

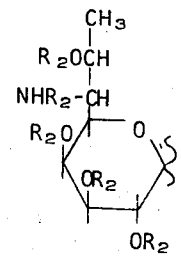

wherein $R_2$ is H or acetyl, and

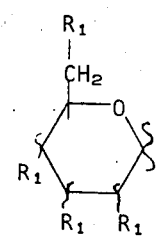

wherein $R_1$ is as defined immediately above; excluding kanamycin A, kanamycin B, kanamycin C, nebramycin factor 4, nebramycin factor 5' and tobramycin.

The structural formulae for kanamycin A, kanamycin B, kanamycin C, nebramycin factor 4, nebramycin factor 5' and tobramycin are as follows:

| Kanamycin A | $R_1=NH_2$ | $R_2=OH$ | Nebramycin factor 4 | $R_1=OH$ | $R_2=\overset{O}{\overset{\|}{C}}NH_2$ |
|---|---|---|---|---|---|
| Kanamycin B | $R_1=NH_2$ | $R_2=NH_2$ | Nebramycin factor 5' | $R_1=H$ | $R_2=\overset{O}{\overset{\|}{C}}NH_2$ |
| Kanamycin C | $R_1=OH$ | $R_2=NH_2$ | Tobramycin | $R_1=H$ | $R_2=H$ |

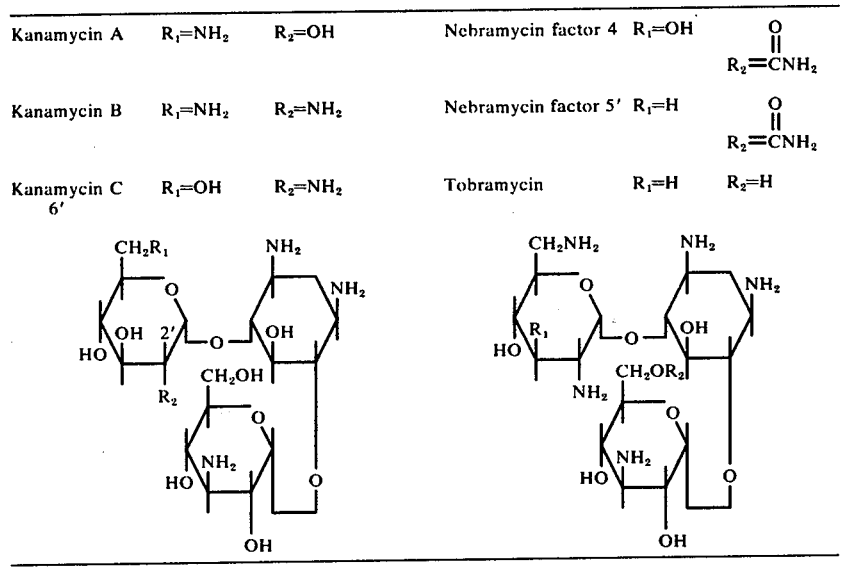

A sub-generic group of the novel compounds depicted supra can be shown as follows:

Paromamine
|
G wherein G is a glycosyl attached to the 3' or 6 position of paromamine, said glycosyl of the formulae

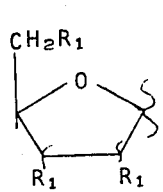 OR 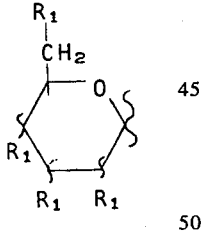

wherein $R_1$ is selected from the group consisting of OAc, OH, NHAc, or $NH_2$; and wherein Ac is acetyl.

Another sub-generic group of the novel compounds depicted supra can be shown as follows:

A
|
G wherein A is as defined above and G is a glycosyl attached to the 6 position of A, said glycosyl of the formulae

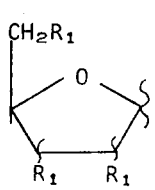 OR 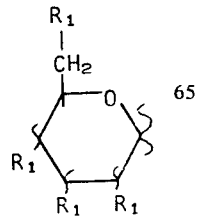

wherein $R_1$ is selected from the group consisting of OAc, OH, NHAc, or $NH_2$; and wherein Ac is acetyl; excluding kanamycin A, kanamycin B, kanamycin C, nebramycin factor 4, nebramycin factor 5' and tobramycin.

Another sub-generic group of the novel compounds depicted supra can be shown as follows:

Paromamine
|
G wherein G is a glycosyl attached to the 3' or 6 position of paromamine, said glycosyl of the formulae

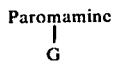 OR 

wherein $R_3$ is H or acetyl.

Another sub-generic group of the novel compounds depicted supra can be shown as follows:

A
|
G wherein A is as defined above and G is a glycosyl attached to the 6 position of A, said glycosyl of the formulae

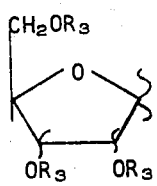 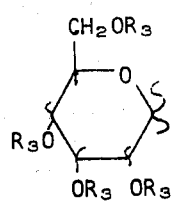

OR wherein $R_3$ is H or acetyl.

The novel intermediates, disclosed herein, are useful to make novel aminoglycoside antibiotics. These novel aminoglycoside antibiotics are antibacterially active, and, thus, they can be used in various environments to eradicate or control sensitive bacteria. Following are in vitro antibacterial test results for representative compounds of the subject invention. The results were obtained with a standard disc plate assay using 12.5 mm paper discs.

Compounds were also tested in a standard microplate test in Brain Heart Infusion (BHI) Agar, at a concentration of 1 mg/ml. Incubation is at 37° and end points are read at 20 hours. Brain Heart Infusion Agar (supplied by Difco Laboratories, Detroit, Michigan, U.S.A.) has the following composition:

| | |
|---|---|
| Calf brains, infusion from | 200 gm. |
| Beef heart, infusion from | 250 gm. |
| Bacto Proteose-peptone, Difco | 10 gm. |
| Bacto-Dextrose, Difco | 1 gm. |
| Sodium chloride | 5 gm. |
| Disodium phosphate | 2.5 gm. |
| Agar | 15 gm. |

| | Minimum Inhibitory Concentration (mcg/ml) | | | | |
|---|---|---|---|---|---|
| Compound | (9) | (7α) | Neamine Control | *(7β) | *Neamine Control |
| Organism | | | | | |
| S. aureus 284 UC 76 | 125 | 1000 | 125 | 1000 | 62.5 |
| S. aureus UC 570 | 250 | 500 | 250 | 1000 | 62.5 |
| S. aureus UC 746 | 250 | 1000 | 250 | 500 | 62.5 |
| S. hemolyticus UC 152 | 3.9 | 31.2 | 3.9 | 62.5 | 7.8 |
| St. faecalis UC 694 | >1000 | >1000 | 1000 | >1000 | 500 |
| E. coli UC 45 | 250 | 500 | 62.5 | 500 | 125 |
| P. vulgaris UC 93 | 500 | 1000 | 250 | 500 | 125 |
| K. pneumoniae UC 58 | 62.5 | 62.5 | 7.8 | 62.5 | 15.6 |
| S. schottmuelleri UC 126 | 250 | 500 | 62.5 | 250 | 62.5 |
| Ps. aeruginosa UC 95 | >1000 | >1000 | >1000 | >1000 | >1000 |
| D. pneumoniae UC 41 | >1000 | >1000 | >1000 | >1000 | >1000 |

*Run on different day from other samples.
NOTE:
UC is a registered trademark designating The Upjohn Company Culture Collection.

| Compound Tested | Zone of Inhibition (mm) | | | |
|---|---|---|---|---|
| | B. cereus | | B. subtilis | |
| | 5 mg/ml* | 10 mg/ml* | 5 mg/ml* | 10 mg/ml* |
| (7β) | 25 | 34 | 35 | 38 |
| (7α) | 25 | 32 | 32 | 34 |
| (9) | 29 | 34 | 32 | 34 |
| (11) | — | 16 | — | — |

*Concentration of Compound Tested.

Compounds (7β), (7α) and (9) were tested again along with compounds (11) and (14β) against a neamine control using the same conditions as given above. These results are shown in the following table.

| | Minimum Inhibitory Concentration (mcg/ml) | | | | | | |
|---|---|---|---|---|---|---|---|
| Compound | (9) | (11) | (7α) | Neamine Control | (7β) | (14β) | Neamine Control |
| Organism | | | | | | | |
| S. aureus UC 76 | 125 | 1000 | 62.5 | 31.2 | 500 | 1000 | 31.2 |
| S. hemolyticus UC 152 | 3.9 | 1000 | 7.8 | 2.0 | 250 | 1000 | 3.9 |
| S. faecalis UC 694 | 1000 | 1000 | 1000 | 500 | 1000 | 1000 | 500 |
| D. pneumoniae UC 41 | 125 | 1000 | 125 | 62.5 | 1000 | 1000 | 31.2 |
| E. coli UC 45 | 250 | 1000 | 62.5 | 62.5 | 1000 | 1000 | 62.5 |
| K. pneumoniae UC 58 | 31.2 | 1000 | 7.8 | 7.8 | 250 | 500 | 3.9 |
| S. schottmuelleri UC 126 | 62.5 | 1000 | 125 | 62.5 | 500 | 1000 | 31.2 |
| Ps. aeruginosa UC 95 | 1000 | 1000 | 1000 | 1000 | 1000 | 1000 | 1000 |
| P. vulgaris UC 93 | 125 | 1000 | 125 | 15.6 | 1000 | 1000 | 62.5 |
| P. mirabilis A-63 | 500 | 1000 | 500 | 250 | 1000 | 1000 | 250 |
| P. morgani UC 3186 | 125 | 1000 | 125 | 31.2 | 1000 | 1000 | 62.5 |
| P. rettgeri UC 339 | 1000 | 1000 | 1000 | 500 | 1000 | 1000 | 1000 |
| S. marcescens UC 131 | 500 | 1000 | 250 | 125 | 1000 | 1000 | 250 |
| S. flexneri UC 143 | 500 | 1000 | 125 | 62.5 | 1000 | 1000 | 62.5 |
| S. typhi TG-3 | 250 | 1000 | 62.5 | 31.2 | 1000 | 1000 | 15.6 |

Compound (14β) was also tested against a series of bacteria on a standard agar disc plate assay, as described above. These results are as follows:

| Agar Diffusion Assay of 3'-O-β-D-Ribosylneamine (14β) | | | |
|---|---|---|---|
| Dilutions | B. cereus UC 3145 | B. subtilis UC 564 | S. aureus UC 76 |
| Full Strength | 25.5 | 37 | 25 |
| 1 : 2 | 24 | 35.5 | 23 |
| 1 : 4 | 21 | 33 | 21 |
| 1 : 8 | 18 | 30.5 | 17.5 |
| Dilutions | p. vulgaris UC 93 | Ps. aeruginosa UC 95 | E. coli UC 51 |
| Full Strength | 26 | 20 | 27 |
| 1 : 2 | 22 | 17 | 24.5 |
| 1 : 4 | 19.5 | 14 | 22 |
| 1 : 8 | 16 | — | 18 |
| Dilutions | S. lutea UC 130 | K. pneumoniae UC 57 | |
| Full strength | 25 | 31 | |
| 1 : 2 | 22.5 | 29 | |
| 1 : 4 | 19 | 27 | |
| 1 : 8 | 15 | 23 | |

From the above results, it is seen that compounds (7α), (7β), (9), (11) and (14β) are active against Bacillus cereus and, thus, these compounds can be used to to treat woolen felts since B. cereus has been isolated from deteriorated woolen felts in the paper industry. Compounds (7α), (7β), (9) and (14) are active against Bacillus subtilis, and, thus, these compounds can be used for controlling the infection of silkworms caused by B. subtilis; further, these compounds can be used to minimize or prevent odor in fish and fish crates caused by B. subtilis. Compounds (5α), (5β), (9) and (14β) are active against Staphylococcus aureus, and, thus, these compounds can be used as disinfectants on washed and stacked food utensils contaminated with S. aureus. Compounds shown to be active against Escherichia coli can be used to reduce, arrest, and eradicate slime production in papermill systems caused by this bacterium; they also can be used to prolong the life of cultures of Trichomonas foetus, Trichomonas hominis, and Trichomonas vaginalis by freeing them of E. coli contamination. Further, since some of the compounds are active against Streptococcus hemolyticus, as shown above, they can be used to disinfect instruments, utensils, or surfaces, where the inactivation of this microorganism is desirable. Evidence of antibacterial activity against other bacteria, as shown above, is sufficient to enable the skilled artisan to use the compounds in a number of environments which are well known to be inhabited by such bacteria.

Salts of the novel aminoglycoside antibiotics, disclosed herein, can be made by reacting the parent antibiotic with a stoichiometric amount of a nontoxic, pharmaceutically acceptable acid. Examples of such acids are acetic, hydrochloric, sulfuric, maleic, phosphoric, nitric, hydrobromic, ascorbic, malic, citric, and like acids used to make salts of amine-containing antibiotics.

The following examples are illustrative of the process and products of the present invention but are not to be construed as limiting. All percentages are by weight and all solvent mixture proportions are by volume unless otherwise noted. Temperatures are in centigrade.

The test data in the following preparation and Examples was obtained as follows. Melting points were taken in a Thomas-Hoover m.p. apparatus. Infrared (ir) absorption spectra were recorded from mineral oil mulls on a Perkin-Elmer Infracord spectrophotometer. Proton magnetic resonance (pmr) spectra were recorded on a Varian A-60 spectrophotometer; all samples were dissolved in deutero-acetone unless otherwise stated with tetramethylsilane as an internal standard. Chemical shifts are reported as δ values (TMS 0.0). Optical rotations were observed at 25° in the solvents noted at a concentration of 1%. Analtech (3 in. or 8 in.) tlc plates coated with silica gel G were used for tlc; visualization was obtained by $H_2SO_4$ charring unless stated otherwise. Tlc system J-18 is the upper layer from equilibration of chloroform, methanol, concentrated $NH_4OH$, water (25:25:3:47). Column chromatography used Silica Gel 60 (EM Reagents, Elmsford, N.Y.). Fractions were monitored by tlc and combined on the basis of the tlc profile.

Preparation of 2,3,5-Tri-O-acetyl-β-D-ribofuranosyl bromide

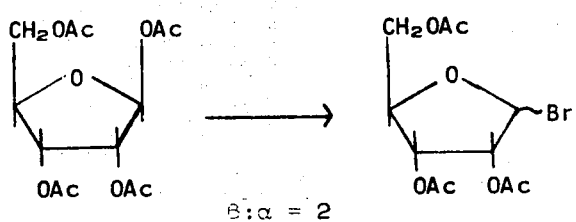

Hydrogen bromide is passed for two minutes through a solution of 1.908 g (6 mmol) of 1,2,3,4-tetra-acetyl-β-D-ribofuranose at ambient temperature. The solvent is distilled under vacuum. The residue is dissolved in 5 ml of toluene and then this solvent is removed at 1 mmol with a bath temperature of 40°. This treatment is repeated. Tlc on silica gel using chloroform-methanol (20:1) shows a very strong spot ($H_2SO_4$) at $R_f$ 0.5 with a weak spot slower and a trace near the front. (1,2,3,4-Tetra-acetyl-β-D-ribofuranose) gives an $R_f$ of 0.9 on this system. Pmr (CDCL₃) δ2.05–2.10 (3 singlets, COCH₃), 6.36 (s, anomeric α H), 6.7 (d, 4, anomeric βH) indicates a ratio of about 2:1 in favor of a β-bromide (α-hydrogen) at C-1. The bromide is used without further purification.

EXAMPLE 1

1,2',3,6'-Tetrakis-N-(trifluoroacetyl)neamine (2)

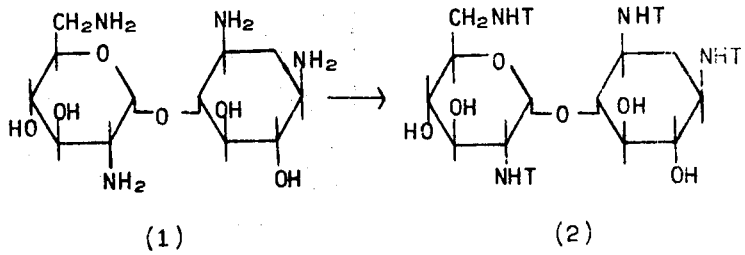

Trifluoroacetic anhydride (33.5 ml, 160 mmol) is added at 15° ± 5° over a period of 30 minutes to a suspension of 9.66 g (30 mmol) of neamine in 100 ml of acetonitrile and 22.4 ml (160 mmol) of triethylamine. After stirring at ambient temperature for 1 hour the solvent is evaporated in vacuo. The residue is diluted with 150 ml of ethyl acetate. The resulting solution is washed with 5% KHCO$_3$ — saturated NaCl (1:1) several times, dried and concentrated. The residue is triturated with ether and the crystals recrystallized from ethanol to give 15.95 g (75.3%) of (2), m.p. 286°–288° dec. An additional 1.2 g (5.2%) of (2), melting at 278°–280°, is obtained from the mother liquors. A portion is recrystallized twice from ethanol to afford an analytical sample, m.p. 304°–306°; [α]$_D$ +63° (EtOH); ir 3600–3300 cm$^{-1}$ (NH/OH), 1700 (C=O), 1560 (amide II), 1220, 1180, 1160 (CF/C-O); pnr δ5.28 (d, 3, anomeric), 3.2–4.2 (cluster); mass spectrum (TMS deriv.) m/e 974 (M-15), 497, 481.

Anal. Calcd. for C$_{20}$H$_{22}$F$_{12}$N$_4$O$_{10}$: C, 34.00; H, 3.14; N, 7.93; F, 32.28. Found: C, 33.76; H, 3.18; N, 8.12; F, 32.25.

EXAMPLE 2

5,6-O-Isopropylidene-1,2',3,6'-tetrakis-N-(trifluoroacetyl) neamine (3) and
3',4',5,6-O-Diisopropylidene-1,2',3,6'-tetrakis-N-(trifluoroacetyl)neamine (3a)

A mixture of 7.06 g (10 mmol) of 1,2',3,6'-tetrakis-N-(trifluoroacetyl)neamine (2) in 30 ml of acetonitrile and 60 ml of dimethoxypropane containing 0.25 ml of trifluoroacetic acid is heated at reflux for 0.75 hour. Amberlite IRA-45 (OH$^-$) resin (12 g) supplied by Rohm and Haas Co., is added to the cooled solution with stirring. After 10 minutes a neutral reaction is obtained on moist acid-base indicator paper. The solution is filtered and concentrated under vacuum. Chromatography over 500 g of silica gel using chloroform methanol (10:1) for elution leads to the isolation of 5.68 g (76.25%) of noncrystalline monoketal (3). Rechromatography gives a sample having the following data: [α]$_D$ +75° (EtOH); ir 3430, 3300, 3100 cm$^{-1}$ (NH/OH), 1705 (C=O), 1560 (amide II), 1215, 1185, 1160 (CF$_3$/c-O), pnr δ5.35 (d, 3, anomeric), 3.2–4.7 (cluster), 1.36 (S, >C(CH$_3$)$_2$.

Anal. Calcd. for C$_{23}$H$_{26}$F$_{12}$N$_4$O$_{10}$: C, 37.00; H, 3.51; N, 7.51. Found: C, 36.72; H, 3.64; N, 7.58.

In addition to monoketal (3) a less polar fraction of 1.02 g (12.95%) is also collected. Physical data indicates this to be diketal (3a): mass spectrum m/e 771 (M—CH$_3$), 767 (M—F), 728 (M—(CH$_3$)$_2$CO), 717 (M—CF$_3$), 673 (M—CF$_3$CONH$_2$), 377, 393; pmr δ5.48 (d, 3, anomeric), 3.2–4.5 (cluster), 1.4 (S, 2 >C(CH$_3$)$_2$).

EXAMPLE 3

5,6-O-Isopropylidene-3',4'-bis-O-(p-nitrobenzoyl)-1,2',3,6'-tetrakis-N-(trifluoroacetyl)neamine (4)

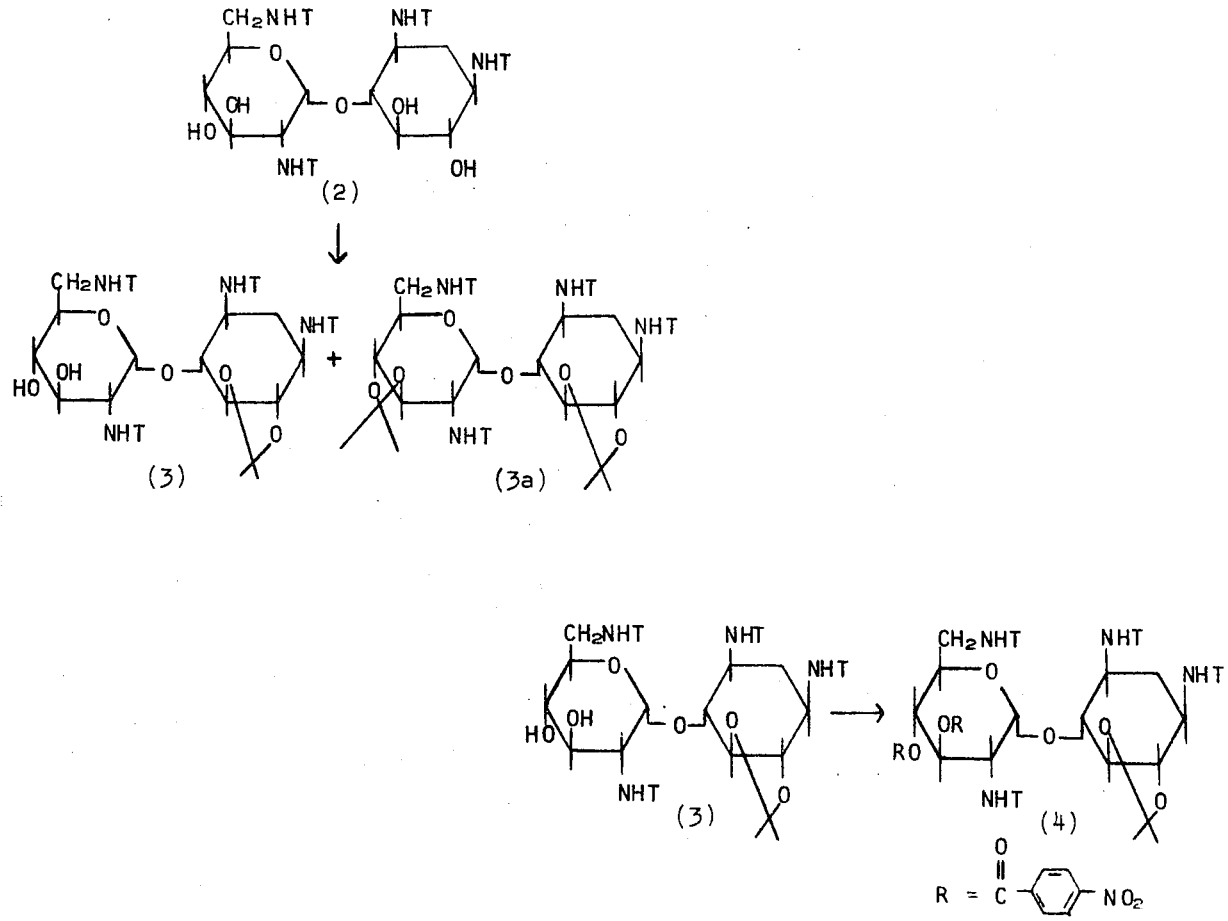

p-Nitrobenzoyl chloride (34.8 g, 0.19 mole) is added to a solution of 36.0 g (0.048 mole) of ketal (3) in 420 ml of pyridine while cooling so that the temperature remains below 35°. After stirring for 2.5 hours at ambient temperature the pyridine is distilled under vacuum. The residue is dissolved in ethyl acetate and washed successively with dilute HCl, H$_2$O and KHCO$_3$ solution. The residue after evaporation of the solvent weighs 63.7 g. Chromatography over 5 kg of silica gel using chloroform-methanol (40:1) for elution affords 47.5 g (94.2%) of solid (4); [α]$_D$ —32° (acetone).

Anal. Calcd. for C$_{37}$H$_{32}$F$_{12}$N$_6$O$_{16}$: C, 42.53; H, 3.09; N, 8.05. Found: C, 42.19; H, 3.01; N, 7.93.

EXAMPLE 4

3',4'-Bis-O-(p-nitrobenzoyl)-1,2',3,6'-tetrakis-N-(trifluoroacetyl)neamine (5)

tion of 35.4 g (80.7%) of diester (5) is obtained. It shows [α]$_D$ acetone —43°; UV in EtOH λ max = 258 mμ (ε 26,700); ir in mineral oil mull, max bands at 3250–3400 cm$^{-1}$ (NH/OH), 1705, 1750 (C=O), 1620 (C = C), 1575 (amide II), 1220, 1180, 1160 (CF$_3$/C:O); pmr δ 8.0–8.3 (aromatic), 5.64 (d, 3, anomeric), 3.2–4.3 (cluster).

Anal. Calcd. for C$_{34}$H$_{28}$F$_{12}$N$_6$O$_{16}$: C, 40.65; H, 2.81; N, 8.37. Found: C, 40.84; H, 2.96; N, 8.36.

EXAMPLE 5

3',4'-Bis-O-(p-nitrobenzoyl)-6-O-(2,3,5-tri-O-acetyl-α-D-ribofuranosyl)-1,2',3,6'-tetrakis-N-(trifluoroacetyl) neamine (6α) and 3',4'-bis-O-(p-nitrobenzoyl)-6-O-(2,3,5-tri-O-acetyl-β-D-ribofuranosyl)-1,2',3,6'-tetrakis-N-(trifluoroacetyl)-neamine (6β)

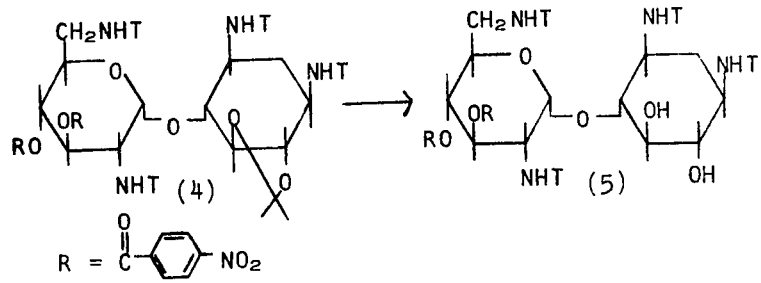

A solution of 45.5 g (43.6 mmol) of ketal (4) in 450 ml of 66% acetic acid solution is warmed at 65° for 4 hours. The reaction mixture is lyophilized. The residue of 37.6 g is chromatographed over 3.5 kg of silica gel using chloroform-methanol (10:1) for elution. A frac- Benzene (50 ml) is distilled from a solution of 6.0 g (6 mmol) of diester (5) in 100 ml of purified nitromethane and 150 ml of benzene. 2,3,5-O-Triacetyl-D-ribofuranosyl bromide (prepared as described above from 11.8 mmol of tetraacetate) in 6 ml of nitromethane and 2.98 g (11.8 mmol) of Hg(CN)$_2$ are added. Further additions of a total of 45.4 mmol of bromide and 8.94 g of Hg(CN)$_2$ are made in two additions with about 2 hours of reflux between additions. Tlc (chloroformmethanol, 20:1) shows the absence of starting diester (5). Ethyl acetate (250 ml) is added and the solution extracted twice with KHCO$_3$ solution. The dried solution is concentrated under vacuum. Chromatography over 2 kg of silica gel using chloroform-methanol (30-1) for elution followed by rechromatography of fractions which are mixtures, gives 4.6 g (60.77%) of (6β) and 1.9 g (25%) of (6α). Rotations of −2° and −46° (acetone) are found for (6α) and (6β), respectively.

Anal. Calcd. for C$_{45}$H$_{42}$N$_6$F$_{12}$O$_{23}$: C, 42.80; H, 3.35; N, 6.66. Found: (6α) C, 42.81; H, 3.53; N, 6.72; (6β) C, 42.85; H, 3.35; N, 6.55.

EXAMPLE 6

6-O-(β-D-Ribofuranosyl)neamine (7β)

testing vs. B. cereus and tlc using system J-18. The results are summarized below.

| Fraction No. | Zone Size (m mol) | Tlc Assay |
|---|---|---|
| 1-2 | — | — |
| 3-5 | — | (orange color, UV$^+$) |
| 6-23 | — | — |
| 24,25 | tr | — |
| 26 | 23 | 1 spot |
| 27 | 29 | max. intensity |
| 28 | 28 | max. intensity |
| 29 | 24 | weaker |
| 30 | 21 | — |
| 31 | 20 | — |
| 32 | 17 | — |
| 33-35 | — | — |

Fractions 26-29 are combined and lyophilized to give 460 mg (58.7%) of 7β. Fractions 30-32 similarly yields 20 mg. Ir (Nujol) 3100-3500 cm$^{-1}$ (NH/CH), 1600 (NH).

EXAMPLE 7

6-O-(α-D-Ribofuranosyl)neamine (7α)

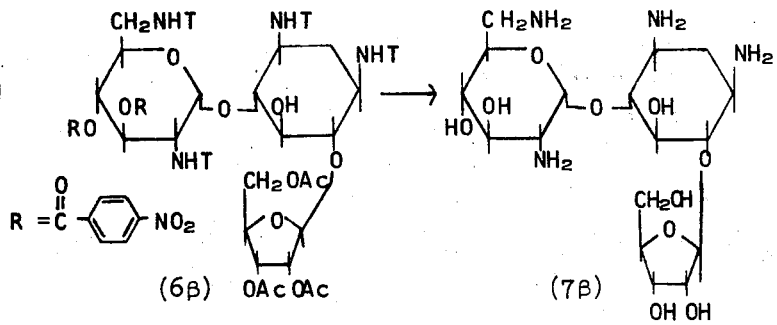

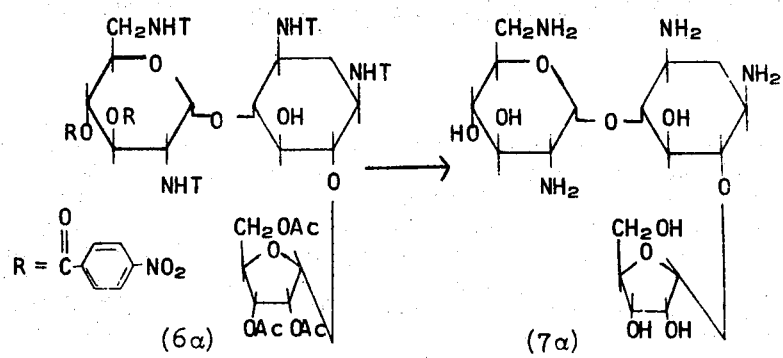

A solution of 2.17 g (1.72 mmol) of glycoside (6β) and 1.24 g (30.96 mmol) of NaOH in 15 ml of methanol and 15 ml of water is heated at reflux for 15 minutes. The methanol is removed in vacuo. Water (75 ml) is added and the solution passed through 10 ml of Amberlite CG-50 (NH$_4$$^+$) resin, supplied by Rohm and Haas Co. The column is washed with 100 ml H$_2$O and then is eluted with a gradient of 400 ml each of water and 0.5N NH$_4$OH. Fractions of about 40 ml are collected. The fractions are monitored by dipped disc In the manner described for the β-isomer, 500 mg of glycoside recovered from physical measurements is treated with 200 mg of NaOH and passed over CG-50 (NH$_4$$^+$) to give 94 mg (53%) of (7α).

EXAMPLE 8

6-O-(dihydrogen orthoacetyl)-3',4'-bis-O-(p-nitrobenzoyl)-1,2',3,6'-tetrakis-N-(trifluoroacetyl)neamine, cyclic ester with 3,5-di-O-acetyl-α-D-ribofuranose (8)

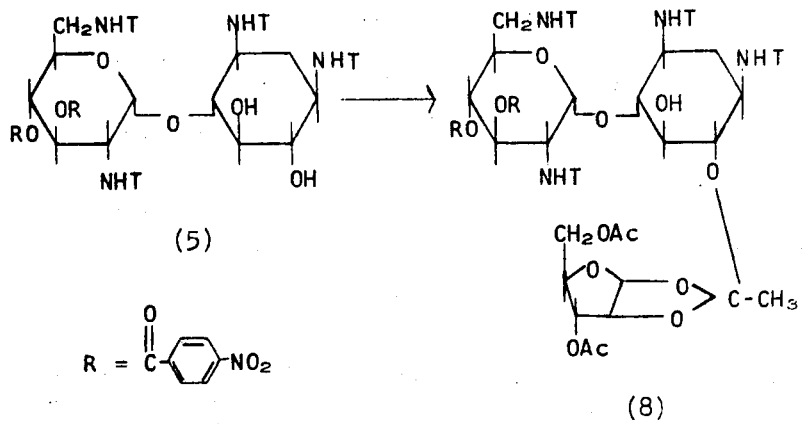

(5)

R = <chemical structure: C(=O)-C6H4-NO2>

(8)

A solution of 3 g (3 mmol) of diol (5), 0.84 ml (6 mmol) of triethylamine and 3 mmol of 2,3,5-tri-O-acetyl-D-ribofuranosyl bromide in 140 ml of tetrahydrofuran is heated at reflux. Tlc using chloroform-methanol (20:1) indicates a new faster spot after 1 hour. Three additions of 3 mmol of bromide and 0.84 ml (6 mmol) of triethylamine are made at hourly intervals. The reaction mixture is refluxed an additional 4 hours, filtered and evaporated. The residue is chromatographed over 450 g of silica gel using chloroform-methanol (40-1) for elution. The product fraction weighs 2.10 g (55.6%). Diol (5) is recovered (977 mg) by stripping the column with chloroform-methanol, 10:1. The orthoester (8) gives the following data: $[\alpha]_D$ −8° (acetone); ir, 3200–3600 cm$^{-1}$ (NH/OH), 1720–1770 (C = O), 1640 (C = C), 1550 (amide II); pmr, δ (DMF) 7.7–8.2 -bis-(dimethylamino)-naphthalene (aromatic), 5.78 (d, 3, anomeric), 3.3–4.1 (cluster), 7.8 (S, COCH$_3$, CH$_3$) 7.4 (S, COCH$_3$).

Anal. Calcd. for $C_{45}H_{42}F_{12}N_6O_{23}$: C, 42.80; H, 3.35; N, 6.66. Found: C, 42.41; H, 3.19; N, 6.34.

A similar product is obtained in 50% yield when 1,4-bis-(dimethylamino) is used instead of triethylamine.

EXAMPLE 9

6-O-Dihydrogen orthoacetylneamine, cyclic ester with 3,5-di-O-acetyl-α-D-ribofuranose (9)

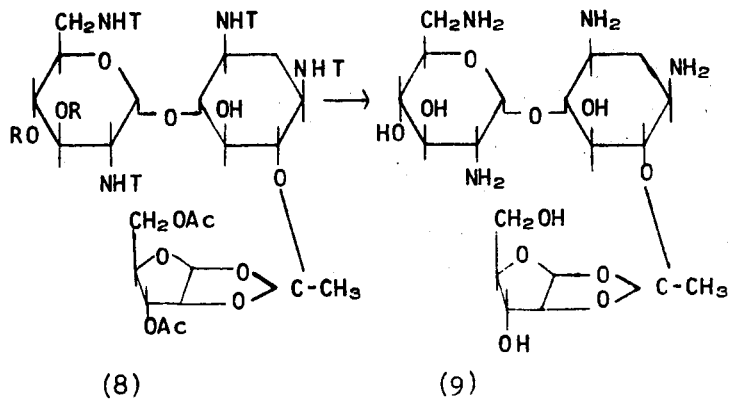

(8)        (9)

Orthoester (8) (1.26 g, 1 mmol) in 9 ml of H$_2$O and 9 ml MeOH containing 720 mg (18 mmol) of NaOH is refluxed for 15 minutes. The methanol is evaporated. The aqueous residue is diluted with 50 ml H$_2$O and passed through 60 ml of CG-50 (NH$_4^+$). The column is eluted with a gradient of 200 ml H$_2$O and 200 ml of 0.5 N NH$_4$OH. Fractions of 20 ml are collected. They are assayed on tlc (J-18) and by dipped disc vs. B. cereus. Fractions 12–25 are combined on the basis of bioactivity and tlc data and then lyophilized. There are thus obtained 406 mg of orthoester (9), ir (Nujol), 3100–3500 (NH/CH), 1600 (NH) (similar to neamine).

EXAMPLE 10

5,6-O-isopropylidene-3'-O-(2,3,4,6-tetrakis-O-acetyl-β-D-glucopyranosyl)-1,2',3,6'-tetrakis-N-(trifluoroacetyl) neamine (10) and 5,6-O-Iisopropylidene 3'-O-(2,3,4,6-tetrakis-O-acetyl-α-D-glucopyranosyl)-1,2',3,6'-tetrakis-N-(trifluoroacetyl) neamine (10α)

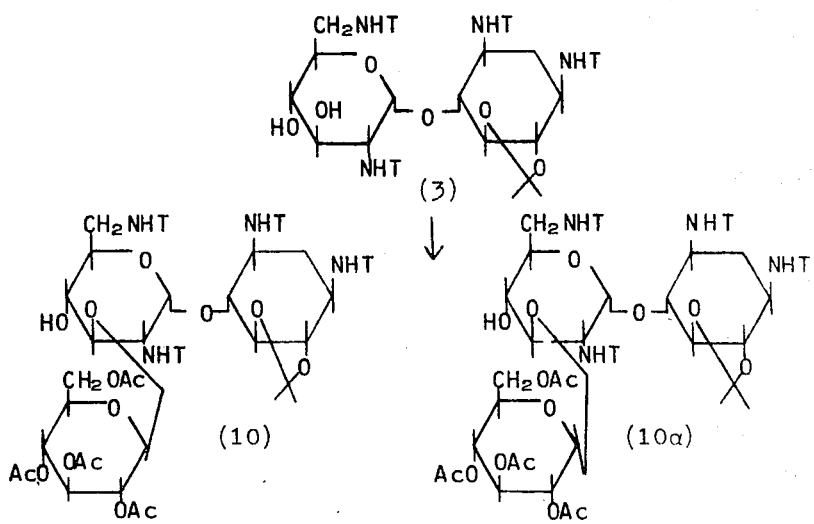

Twenty-five ml of benzene is distilled from a solution of 3.73 g (5 mmol) of ketal (3) in 50 ml of purified $CH_3NO_2$ and 75 ml of benzene. α-Acetobromoglucose (4.10 g, 10 mmol) and 2.5 g, 10 mmol of $Hg(CN)_2$ are added and refluxed for 2 hours. Two more additions of bromide and base are made at 2 hour intervals. The solvent is distilled under vacuum. The residue is dissolved in ethyl acetate, filtered, and washed with $KHCO_3$ three times. Filtration is necessary to remove mercuric salts. The solution is dried and evaporated to give a residue of 14.3 g. This material is chromatographed over 0.75 kg of silica gel eluting with chloroform-methanol (20:1). A fraction of 5.03 g showing at least four components by tlc and a more polar fraction of 1.66 g (one component) is obtained. The latter shows in the ir spectrum bands at 1740 and 1550 cm$^{-1}$ indicative of ester and amide. On the bssis of the mobility and ir data it is characterized as glycoside (10).

EXAMPLE 11

3′-O-(2,3,4,6-Tetra-O-acetyl-β-D-glucopyranosyl)-1,2′,3,6′-tetrakis-N-(trifluoroacetyl)neamine (10X)

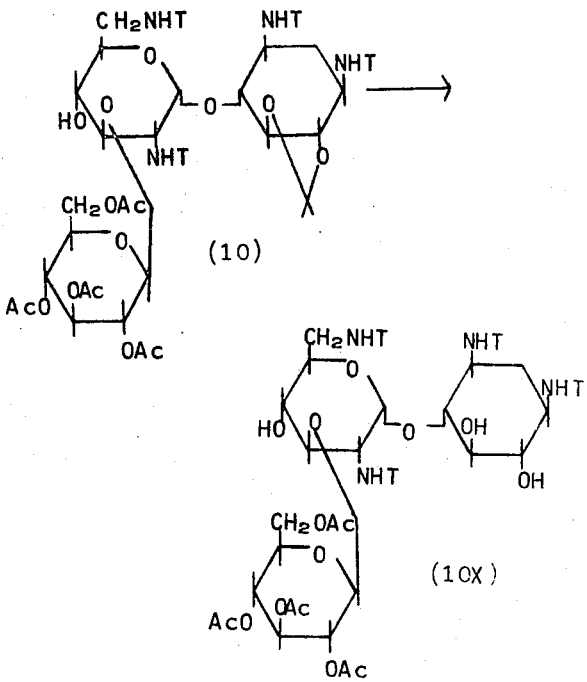

A solution of 1.6 g of glycoside (10) is dissolved in 30 ml of 66% HOAc and the mixture is heated at 65° for 2.5 hours. The solution is lyophilized. Tlc (chloroform-methanol, 10:1) shows no (10) but a slower spot (10X).

EXAMPLE 12

3′-O-(β-D-glucopyranosyl)neamine (11)

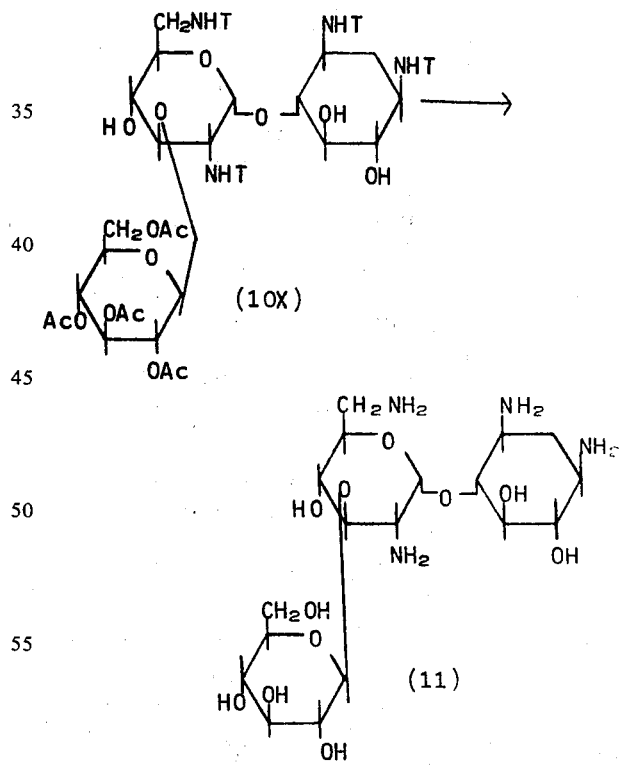

Glycoside (10X) (1.11 g) and 720 mg of NaOH in 9 ml of MeOH and 9 ml of $H_2O$ are refluxed for 15 minutes. The methanol is evaporated in vacuo. The aqueous solution is put over 50 ml of CG-50 ($NH_4^+$). The column is eluted with 50 ml $H_2O$ and then with a gradient of 200 ml $H_2O$ and 200 ml of 0.5N $NH_4OH$. A fraction of 390 mg is obtained which seems to be one spot on silica gel tlc (J-18, ninhydrin).

using the dipped disc technique, glycoside (11) at 10 mg/ml, gives a 16 mmol zone of inhibition vs. B. cereus. Neamine at 10 mg/ml gives a 32 mmol zone and at 5 mg/ml a 29 mmol zone.

EXAMPLE 13

5,6-O-Isopropylidene-3'-O-(2,3,5,-tri-O-acetyl-62-D-ribofuranosyl)-1,2',3,6'-tetrakis-N-(trifluoroacetyl) neamine (12β)

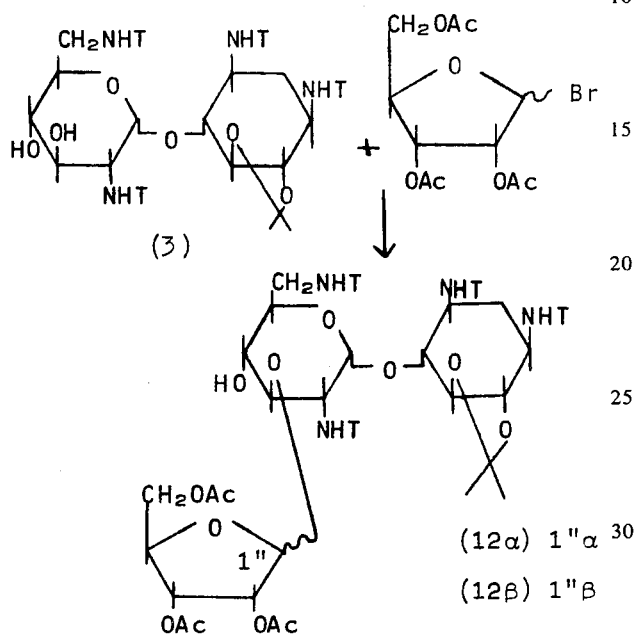

A solution of 10 g of 5,6-O-isopropylidene-1,2',3,6'-tetrakis-N-(trifluoroacetyl)neamine (3) in 330 ml of benzene and 220 ml of nitromethane is heated to boiling and 110 ml of distillate collected. 2,3,5-Tri-O-acetyl-β-D-ribofuranosyl bromide is prepared from 16.5 g of 1,2,3,5-tetra-O-acetyl-β-D-ribofuranose, as described above. The bromide is dissolved in 30 ml of nitromethane. One third of this solution and 7 g of mercuric cyanide is added to the original reaction mixture. The mixture is heated to reflux. Two similar additions of bromide and mercuric cyanide are made after 1 and 2 hours of reflux. The mixture is refluxed a final hour. The cooled reaction mixture is diluted with 750 ml of ethyl acetate and extracted with two 500 ml portions of 5% KHCO₃ solution. The organic layer is washed with brine and filtered through Na₂SO₄. The solvent is evaporated under vacuum. The residue is chromatographed over 1 kg of silica gel, and eluted with chloroform-methanol (20:1). Fractions of 50 ml are collected and monitored by tlc. Fractions 1–30 contain fast moving impurities and are discarded. Fractions 30–40 (27A) weigh 13.4 g, while fractions 41–48 (27B) weigh 3.23 g. A 12.4 g portion of 27A is rechromatographed over 1 kg of silica gel using chloroform-methanol (30:1) for elution. The center cut based on tlc of the fractions is combined and evaporated to give 6.66 g of blocked analog (12β). CMR data, after removal of the blocking group as described infra, shows this compound to be chiefly the 3' β isomer.

EXAMPLE 14

3'-O-(2,3,5-tri-O-acetyl-β-D-ribofuranosyl)-1,2',3,6'-tetrakis-N-(trifluoroacetyl)neamine (13β)

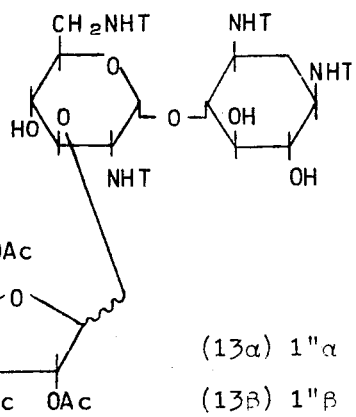

A solution of 6.66 g of (12β) in 40 ml of acetic acid and 20 ml of water is heated at reflux for 2 hours. The solvent is removed by lyophilization. The residue of 5.038 g is used in the next step, Example 15, without purification.

EXAMPLE 15

3'-O-(β-D-Ribofuranosyl)neamine (14β)

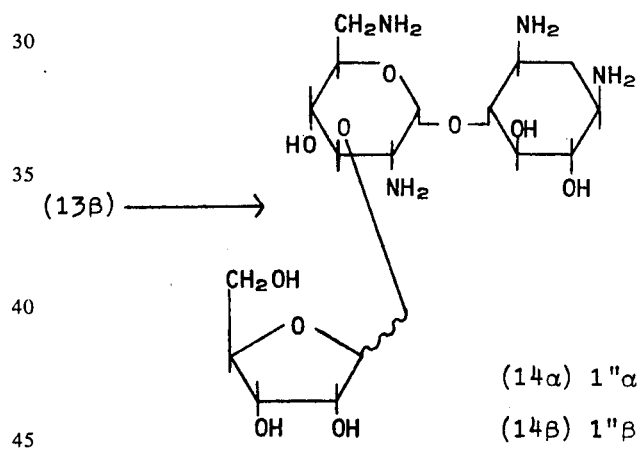

The residue from Example 14 is dissolved in 73 ml of methanol-water (1:1) containing 2.93 g of NaOH. The solution is refluxed for 0.5 hour, cooled and 12 ml of N HCl is added. The methanol is evaporated under vacuum. The aqueous residue is diluted with 200 ml of water and passed through 250 ml of Amberlite CG-50 (NH₄⁺ form). The column is washed with 250 ml H₂O and then eluted with a gradient composed of 1 l of water and 1 l of 0.5N NH₄OH. Fractions (50 ml) are monitored by inhibition of growth of B. cereus using the dipped disc technique and also by tlc (J-18 system) visualizing with ninhydrin. Fractions having a zone of inhibition of greater than 18 mmol and also showing a good response on tlc are combined and lyophilized. A yield of 1.47 g of white powder is obtained. CMR data indicates this to be chiefly 14β.

EXAMPLE 16

By substituting the 2,3,5-O-triacetyl-D-ribofuranosyl bromide in Example 5 by:

2,3,4,6 Tetra-O-acetyl-β-D-altropyranosyl chloride
2,3,4-Tri-O-acetyl-β-L-arabinopyranosyl chloride
3,4-Di-O-acetyl-2-deoxy-D-ribopyranosyl chloride
2,3,4,6-Tetra-O-acetyl-α-D-galactopyranosyl chloride
2,3,4,6 Tetra-O-acetyl-β-D-galactopyranosyl chloride
2,3,4,6-Tetra-O-acetyl-α-D-glucopyranosyl chloride
2,3,4,6-Tetra-O-benzoyl-α-D-glucopyranosyl chloride
2,3,4,6-Tetra-O-acetyl-β-D-glucopyranosyl chloride
2,3,4,6-Tetra-O-acetyl-α-D-mannopyranosyl chloride
2,3,4,6-Tetra-O-benzoyl-α-D-mannopyranosyl chloride
2,3,4-Tri-O-acetyl-α-L-rhamnopyranosyl chloride
2,3,4-Tri-O-benzoyl-α-L-rhamnopyranosyl chloride
2,3,5-Tri-O-acetyl-α-D-ribofuranosyl chloride
2,3,4-Tri-O-benzoyl-α-D-ribopyranosyl chloride
2,3,4-Tri-O-acetyl-β-D-ribopyranosyl chloride
2,3,4-Tri-O-benzoyl-β-D-ribopyranosyl chloride
2,3,4-Tri-O-acetyl-α-D-xylopyranosyl chloride
2,3,4-Tri-O-acetyl-β-D-xylopyranosyl chloride
2,3,4-Tri-O-acetyl-6-deoxy-α-D-glucopyranosyl chloride
2,3,4-Tri-O-acetyl-β-D-arabinopyranosyl bromide
2,3,4-Tri-O-benzoyl-β-D-arabinopyranosyl bromide
3,4,6-Tri-O-acetyl-2-deoxy-α-D-glucopyranosyl bromide
3,4,6-Tri-O-benzoyl-2-deoxy-α-D-glucopyranosyl bromide
2,3,4-Tri-O-acetyl-6-deoxy-α-D-glucopyranosyl bromide
1,3,4,5-Tetra-O-acetyl-β-D-fructopyranosyl bromide
1,3,4,5-Tetra-O-benzoyl-β-D-fructopyranosyl bromide
2,3,4,6-Tetra-O-acetyl-α-D-galactopyranosyl bromide
2,3,4,6-Tetra-O-acetyl-α-D-glucopyranosyl bromide
2,3,4-Tri-O-acetyl-6-O-benzoyl-α-D-glucopyranosyl bromide
2,3,4-Tri-O-acetyl-6-O-methyl-α-D-glucopyranosyl bromide
6-O-Acetyl-2,3,4-Tri-O-benzyl-α-D-glucopyranosyl bromide
2,3,4,6-Tetra-O-acetyl-α-D-mannopyranosyl bromide
2,3,4,6-Tetra-O-benzoyl-α-D-mannopyranosyl bromide
2,3,4-Tri-O-acetyl-αL-rhamnopyranosyl bromide
2,3,4-Tri-O-benzoyl-α-L-rhamnopyranosyl bromide
2,3,4-Tri-O-acetyl-β-D-ribopyranosyl bromide
2,3,4-Tri-O-benzoyl-β-D-ribopyranosyl bromide
2,3,4-Tri-O-benzoyl-D-xylopyranosyl bromide
2,3,4-Tri-O-acetyl-L-xylopyranoxyl bromide
2,3,4-Tri-O-benzoyl-L-xylopyranoxyl bromide 2-Acetamido-3,4,6-tri-O-acetyl-2-deoxy-β-D-glucopyranosyl bromide
2-Acetamido-3,4,6-tri-O-acetyl-2-deoxy-α-D-glucopyranosyl chloride
2-Acetamido-3,4,6-tri-O-acetyl-2-deoxy-β-D-glucopyranosyl chloride
2-Benzamido-3,4,6-tri-O-benzoyl-2-deoxy-α-D-glucopyranosyl bromide
3,4,6-Tri-O-acetyl-2-benzamido 2-deoxy-α-D-glucopyranosyl chloride
3,4,6-Tri-O-acetyl-2-[(benzyloxycarbonyl)-amino]-2-deoxy-α-D-glucopyranosyl bromide
3,4,6-Tri-O-acetyl-2-deoxy-2-(2,4-dinitroanilino)-α-D-glucopyranosyl bromide
2-Acetamido-3,4-di-O-acetyl-2-deoxy-D-ribofuranosyl chloride
2-Acetamido-3,4,6-tri-O-acetyl-2-deoxy-D-galactopyranosyl bromide
2-Acetamido-3,4,6-tri-O-acetyl-2-deoxy-α-D-galactopyranosyl chloride
3-Acetamido-2,4,6-tri-O-acetyl-3-deoxy-α-D-mannopyranosyl bromide
3-Acetamido-2,4,6-tri-O-acetyl-3-deoxy-α-D-mannopyranosyl chloride
2,4,6-Tri-O-acetyl-3-[(benzyloxycarbonyl)-amino]-3-deoxy-α-D-glucopyranosyl bromide
2,3,4-Tri-O-acetyl-6-[(benzyloxycarbonyl)-amino]-6-deoxy-α-D-glucopyranosyl bromide
2,4,6-Tri-O-acetyl-3-[(benzyloxycarbonyl)-amino]-3-deoxy-D-glucopyranosyl chloride
2,3,4-Tri-O-acetyl-6-[(benzyloxycarbonyl)-amino]-6-deoxy-D-glucopyranosyl chloride
N-Acetyl-2,3,4,7-tetra-O-acetyl-α and β-1 incosaminyl bromides
3-Acetamido-2,4,6-tri-O-benzyl-3-deoxy-glucopyranosyl chloride
2,3,4-Tri-O-benzyl-6(N-benzylacetamido)-6-deoxy-α-D-glucopyranosyl chloride
3-Acetamido-2,4,6-tri-O-acetyl-3-deoxy-glucopyranosyl bromide
3,4,6-Tri-O-acetyl-2-trifluoroacetamido-2-desoxy-α-D-glucopyranosyl bromide there are obtained the corresponding 6-O-glycosyl analogs of neamine having ester and amino protecting groups. These protecting groups are then removed by following the procedure of Example 6 to afford antibacterially active 6-O-glycosyl analogs of neamine.

EXAMPLE 17

By substituting the α-acetobromoglucose in Example 10 by 2,3,5-O-triacetylD-ribofuranosyl bromide there is obtained the corresponding 3'-O-D-glycosyl analog of neamine having ester and amino protecting groups. These protecting groups are then removed by following the procedure of Examples 11 and 12 to afford antibacterially active 3'-O-D-glycosyl analogs of neamine.

EXAMPLE 18

By substituting the α-acetobromoglucose in Example 10 by the glycosyl halides in Example 16, there are obtained the corresponding 3'-O-D-glycosyl analogs of neamine having ester and amino protecting groups. These protecting groups are then removed by following the procedure of Examples 11 and 12 to afford antibacterially active 3'-O-D-glycosyl analogs of neamine.

EXAMPLE 19

1-N-AHBA derivative of the 6-O- and 3'-O-D-glycosyl analogs of neamine, as prepared in the preceding examples, is made by first blocking the 6'-amino of the amino-glycoside by reacting it with N-benzyloxycarbonyloxylsuccinimide in aqueous dimethylformamide to form the 6'-N-carbenzoxyamino glycoside. This compound is then selectively 1-N-acylated with L(−)γ-benzyloxycarbonylamino-α-hydroxybutyric acid, N-hydroxysuccinimide ester in aqueous ethylene glycol dimethyl ether. The carbobenzoxy groups at 6'-N and at the γ-N are then removed by hydrogenolysis using palladium on charcoal as catalyst.

EXAMPLE 20

By substituting the 2,3,5-tri-O-acetyl-D-ribofuranosyl bromide in Example 8 by the glycosyl halides in Example 16, there are obtained the corresponding 6-O-D-glycosyl ortho esters of neamine having ester and amino protecting groups. These protecting groups are then removed by following the procedure of Example 9 to afford antibacterially active 6-O-D-glycosyl ortho esters of neamine.

EXAMPLE 21

By substituting compound (5) in Example 8 by compound (3), there is obtained the cyclic ester with 3,5-di-O-acetyl-α-D-ribofuranose of the 5,6-ketal compound (3). The ketal moiety is removed by following the procedures of Example 4, and the ester and amino protecting groups are removed by following the procedures of Example 9 to afford antibacterially active 3'-O-D ortho esters of neamine.

EXAMPLE 22

By substituting the 2,3,5-tri-O-acetyl-D-ribofuranosyl bromide in Example 8 by the glycosyl halides in Example 16, and compound (5) in Example 8 by compound (3), there are obtained the corresponding ester and amino protected ortho esters of the 5,6-ketal compound (3). The ketal moiety, and the ester and amino protecting groups are removed by the procedures referred to in Example 21 to afford corresponding antibacterially active 3'-O-D-glycosyl ortho esters of neamine.

Preparation of Neamine

Neamine can be prepared from neomycin B by the procedures disclosed in U.S. Pat. No. 2,691,675. It also can be synthesized from paromamine as disclosed by S. Umezawa and K. Tatsuta in Bull. Chem. Soc. Japan, 40 2371–75 (1967).

I claim:
1. A compound of the formula

Paromamine
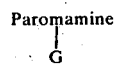
G wherein G is a glycosyl attached to the 3' or 6 position of paromamine, said glycosyl of the formulae

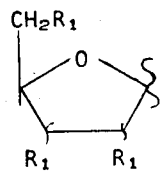

wherein $R_1$ is selected from the group consisting of OH, OAc,

$OCH_2\phi$, NHR', NR' alkyl; wherein alkyl is from 1 to 5 carbon atoms, inclusive; R' is H or acyl of from 1 to 8 carbon atoms, inclusive; Ac is acetyl; and $$\begin{array}{c} CH_3 \\ | \\ R_2OCH \\ | \\ NHR_2-CH \\ R_2O \underset{OR_2}{\overset{O}{\diagup}} \\ OR_2 \end{array}$$

wherein $R_2$ is H or acetyl; and nontoxic pharmaceutically acceptable acid addition salts thereof.

2. A compound of the formula, according to claim 1

Paromamine
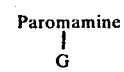
G wherein G is a glycosyl attached to the 3' or 6 position of paromamine, said glycosyl of the formulae

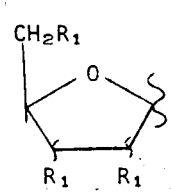

wherein $R_1$ is selected from the group consisting of OAc, OH, NNAc, or $NH_2$; and wherein Ac is acetyl; and nontoxic pharmaceutically acceptable acid addition salts thereof.

3. A compound of the formula, according to claim 2

Paromamine
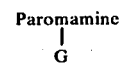
G wherein G is a glycosyl attached to the 3' or 6 position of paromamine, said glycosyl of the formulae

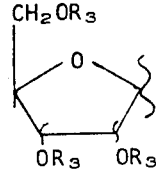

wherein $R_3$ is H or acetyl; and nontoxic pharmaceutically acceptable acid addition salts thereof.

4. A compound of the formula

A
G wherein A is a 4-O-(α-D-glycosyl)-2-deoxystreptamine selected from the group consisting of kanamine, gentamine $C_{1a}$, gentamine $C_1$, gentamine $C_2$, gentamine $C_{2b}$, gentamine B₁, nebramine, and lividamine, and G is a glycosyl attached to the 6 position of said 4-O-(α-D-glycosyl)-2-deoxystreptamine, said glycosyl of the formula

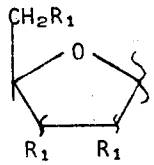

wherein R₁ is selected from the group consisting of OH, OAc,

OCH₂φ, NHR', NR' alkyl; wherein alkyl is from 1 to 5 carbon atoms, inclusive; R' is hydrogen or acyl of from 1 to 8 carbon atoms, inclusive; Ac is acetyl,

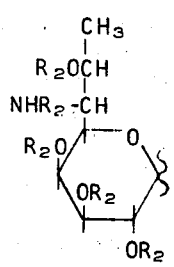

wherein R₂ is H or acetyl, and nontoxic pharmaceutically acceptable acid addition salts thereof.

5. A compound of the formula, according to claim 4

wherein A is as defined in claim 4 and G is a glycosyl attached to the 6 position of A, said glycosyl of the formula

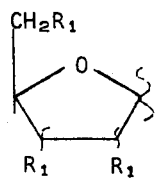

wherein R₁ is selected from the group consisting of OAc, OH, NHAc, or NH₂; and wherein Ac is acetyl; and nontoxic pharmaceutically acceptable acid addition salts thereof.

6. A compound of the formula, according to claim 5

wherein A is as defined in claim 4 and G is a glycosyl attached to the 6 position of A, said glycosyl of the formula

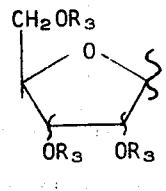

wherein R₃ is H or acetyl; and nontoxic pharmaceutically acceptable acid addition salts thereof.

7. A compound of the formula

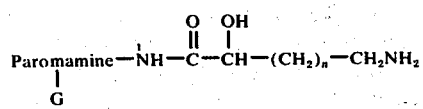

wherein $n$ is an integer of from 0 to 2, inclusive; and G is as defined in claim 1.

8. A compound of the formula

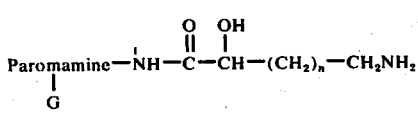

wherein $n$ is an integer of from 0 to 2, inclusive; and G is as defined in claim 2.

9. A compound of the formula

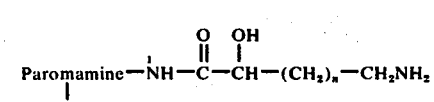

wherein $n$ is an integer of from 0 to 2, inclusive; and G is as defined in claim 3.

10. A compound of the formula

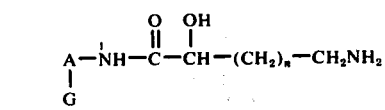

wherein $n$ is an integer of from 0 to 2, inclusive; and A and G are as defined in claim 4.

11. A compound of the formula $$A-NH-\overset{O}{\underset{G}{\overset{\|}{C}}}-\overset{OH}{\overset{|}{C}H}-(CH_2)_n-CH_2NH_2$$

wherein $n$ is an integer of from 0 to 2, inclusive; and A and G are as defined in claim 5.

12. A compound of the formula

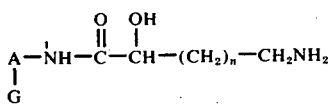

wherein $n$ is an integer of from 0 to 2, inclusive; and A and G are as defined in claim 6.

13. A process for preparing a compound, as defined in claim 4, which comprises:
1. selectively blocking the amino groups on the aglycone,
2. selectively blocking the 5,6-hydroxyls of the amino-protected aglycone to form a ketal,
3. selectively acylating the 3',4'-hydroxyls of the amino-protected aglycone wherein the 5,6-hydroxyls are blocked as the ketal,
4. selectively removing said ketal group to form an amino-protected aglycone having the 3'-4'-hydroxyls acylated,
5. subjecting said acylated amino-protected aglycone to a glycosylation reaction with a glycosyl halide selected from the group consisting of

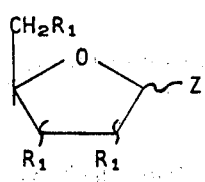 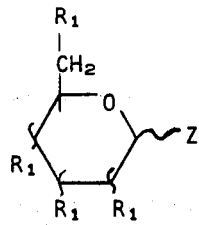

wherein Z is Cl or Br; $R_1$ = OAc,

$OCH_2\phi$, NHR', NR' alkyl; alkyl = 1–5 carbon atoms, inclusive: R' = acyl of from 1 to 8 carbon atoms, inclusive; Ac = acetyl; and

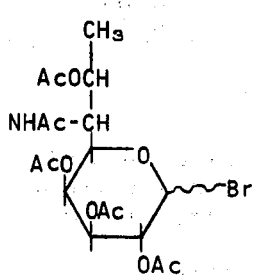

wherein Ac is acetyl, and
6. selectively removing the amino-protecting groups and the acyl moieties to afford the compound, as defined in claim 4.

14. A process, as defined in claim 13, wherein the aglycone amino groups are selectively blocked as the trifluoroacetates.

15. A process, according to claim 13, wherein the said ketal is formed by reacting the amino-protected aglycone in acetonitrile and a dialkoxy lower alkane wherein the alkoxy and lower alkane are from 1 to 8 carbon atoms, inclusive, in the presence of an acid catalyst.

16. A process, according to claim 13, wherein the said selective acylation of the 3' and 4' hydroxyls is conducted with an acylating agent selected from the group consisting of a halide or anhydride of a hydrocarbon carboxylic acid of from 2 to 18 carbon atoms, inclusive; or a halo-, nitro-, hydroxy-, amino-, cyano-, thiocyano-, and lower alkoxy- substituted hydrocarbon carboxylic acid of from 2 to 18 carbon atoms, inclusive, in the presence of an acid-binding agent.

17. A process, according to claim 13, wherein the said 5,6-ketal group is selectively removed by mild acid hydrolysis.

18. A process, according to claim 13, wherein the said glycosylation is conducted under anhydrous conditions using an excess of the glycosyl halide in nitromethanebenzene in the presence of mercuric cyanide.

19. A process, according to claim 13, wherein the said ester and amino-protecting groups are selectively and simultaneously removed with a strong aqueous alkali of about 2N in methanol.

20. A process for preparing the compound of claim 1, wherein the glycosyl is on the 3' position of paromamine, which comprises:
1. selectively blocking the amino groups on paromamine,
2. selectively blocking the 5,6-hydroxyls of the amino-protected paromamine to form a ketal,
3. subjecting said amino-protected paromamine 5,6-ketal to a glycosylation reaction with a glycosyl halide selected from the group consisting of

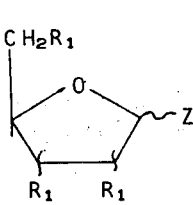 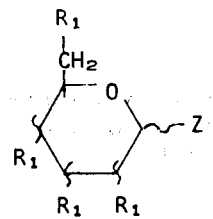

wherein Z is Cl or Br; $R_1$ = OAc,

$OCH_2O$,
NHR', NR' alkyl; alkyl = 1–5 carbon atoms, inclusive; R' = acyl of from 1 to 8 carbon atoms, inclusive; Ac = acetyl; and

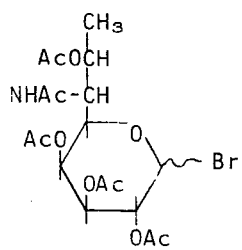

wherein Ac is acetyl, 4. selectively removing the 5,6-ketal moiety, and
5. selectively removing the amino-protecting groups to afford the compound, as defined in claim 1.

21. A process, according to claim 20, wherein the paramamine amino groups are selectively blocked as the trifluoroacetates.

22. A process, according to claim 20, wherein the said ketal is formed by reacting the amino-protected paromamine in acetonitrile and a dialkoxy lower alkane wherein the alkoxy and lower alkane are from 1 to 8 carbon atoms, inclusive, in the presence of an acid catalyst.

23. A process, according to claim 20, wherein the said glycosylation is conducted under anhydrous conditions using an excess of the glycosyl halide in nitromethanebenzene in the presence of mercuric cyanide.

24. A process, according to claim 20, wherein the said 5,6-ketal group is selectively removed by mild acid hydrolysis.

25. A process, according to claim 20, wherein the said amino-protecting groups are selectively removed with a strong aqueous alkali of about 2N in methanol.

26. A process for preparing a compound, as defined in claim 1, wherein the glycosyl is on the 6 position of paromamine, which comprises:
1. selectively blocking the amino groups on paromamine
2. selectively blocking the 5,6-hydroxyls of the amino-protected paromamine to form a ketal,
3. selectively acylating the 3',4'-hydroxyls of the amino-protected paromamine wherein the 5,6-hydroxyls are blocked as the ketal,
4. selectively removing said ketal group to form an amino-protected paromamine having the 3'-4'-hydroxyls acylated,
5. subjecting said acylated amino-protected paromamine to a glycosylation reaction with a glycosyl halide selected from the group consisting of

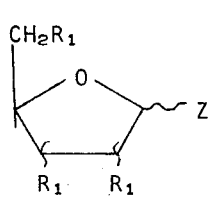 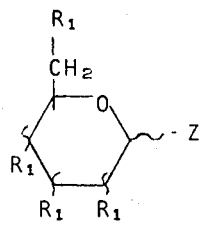

wherein Z is Cl or Br; $R_1 =$ OAc, $$O-C\phi,$$
$$\underset{O}{\|}$$

$OCH_2\phi$, NHR', NR' alkyl; alkyl = 1–5 carbon atoms, inclusive; R' = acyl of from 1 to 8 carbon atoms, inclusive; Ac = acetyl; and

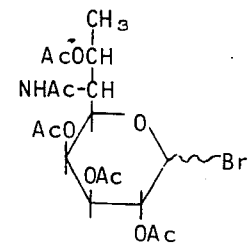

wherein Ac is acetyl, and
6. selectively removing the amino-protecting groups and the acyl moieties to afford the compound, as defined in claim 1.

27. A process, as defined in claim 26, wherein the paromamine amino groups are selectively blocked as the trifluoroacetates.

28. A process, according to claim 26, wherein said ketal is formed by reacting the amino-protected paromamine in acetonitrile and a dialkoxy lower alkane wherein the alkoxy and lower alkane are from 1 to 8 carbon atoms, inclusive, in the presence of an acid catalyst.

29. A process, according to claim 26, wherein the said selective acylation of the 3' and 4' hydroxyls is conducted with an acylating agent selected from the group consisting of a halide or anhydride of a hydrocarbon carboxylic acid of from 2 to 18 carbon atoms, inclusive; or a halo-, nitro-, hydroxy-, amino-, cyano-, thiocyano-, and lower alkoxy-substituted hydrocarbon carboxylic acid of from 2 to 18 carbon atoms, inclusive, in the presence of an acid-binding agent.

30. A process, according to claim 26, wherein the said 5,6-ketal group is selectively removed by mild acid hydrolysis.

31. A process, according to claim 26, wherein the said glycosylation is conducted under anhydrous conditions using an excess of the glycosyl halide in nitromethanebenzene in the presence of mercuric cyanide.

32. A process, according to claim 26, wherein the said ester and amino-protecting groups are selectively and simultaneously removed with a strong aqueous alkali of about 2N in methanol.

* * * * *

UNITED STATES PATENT AND TRADEMARK OFFICE
CERTIFICATE OF CORRECTION

PATENT NO.  : 3,984,393
DATED       : October 5, 1976
INVENTOR(S) : Barney J. Magerlein It is certified that error appears in the above–identified patent and that said Letters Patent are hereby corrected as shown below:

Column 15, lines 62-63, for "-O- and -O-($\alpha$O" read --    --.
Column 21, lines 40-42, for

"

| Zone of Inhibition (mm) | | | |
|---|---|---|---|
| B. cereus | | B. subtilis | |
| 5 mg/ml* | 10 mg/ml* | 5 mg/ml* | 10 mg/ml* |

"

read

--

| Zone of Inhibition (mm) | | | |
|---|---|---|---|
| B. cereus | | B. subtilis | |
| 5 mg/ml* | 10 mg/ml* | 5 mg/ml* | 10 mg/ml* |

--

Column 26, line 16, for "($CF_3$/c-0)" read -- ($CF_3$/C-0) --.
Column 31, line 58, for "7.7-8.2 -bis-(dimethylamino)-naphthalene (aromatic)" read -- 7.7-8.2 (aromatic) --;
line 64, for "(dimethylamino) is" read -- (dimethylamino)-naphthalene is --. Column 32, line 63, for "Iisopropylidene" read -- Isopropylidene --. Column 35, line 1, for "using" read -- Using --; line 7, for "acetyl-62-D" read -- acetyl-$\beta$-D --.
Column 37, line 1, for "acetyl-$\beta$-D" read -- acetyl-$\alpha$-D --;
line 51, for "deoxy-$\beta$-D" read -- deoxy-$\alpha$-D --. Column 39, line 16, for "3'-O-D ortho" read -- 3'-O-D-glycosyl ortho --.
Column 40, Claim 2, line 36, for "NNAc" read -- NHAc --.

Signed and Sealed this

Fourteenth Day of December 1976

[SEAL]

Attest:

RUTH C. MASON
*Attesting Officer*

C. MARSHALL DANN
*Commissioner of Patents and Trademarks*